United States Patent [19]

Duggan et al.

[11] Patent Number: 5,321,034
[45] Date of Patent: Jun. 14, 1994

[54] FIBRINOGEN RECEPTOR ANTAGONISTS

[75] Inventors: Mark E. Duggan, Narberth; George D. Hartman, Landsdale; Nathan Ihle, Perkasie, all of Pa.

[73] Assignee: Merck & Co., Inc., Rahway, N.J.

[21] Appl. No.: 871,261

[22] Filed: Apr. 23, 1992

Related U.S. Application Data

[63] Continuation-in-part of Ser. No. 720,547, Jun. 25, 1991, abandoned, which is a continuation-in-part of Ser. No. 696,904, May 7, 1991, abandoned.

[51] Int. Cl.$^5$ .................. A61K 31/445; C07D 211/28; C07D 401/12
[52] U.S. Cl. .................. 514/323; 514/331; 546/201; 546/233
[58] Field of Search ............... 546/201, 233; 514/323, 514/331

[56] References Cited

U.S. PATENT DOCUMENTS

| | | | |
|---|---|---|---|
| 4,122,255 | 10/1980 | Krapcho | 544/160 |
| 4,243,807 | 1/1981 | Friebe et al. | 546/232 |
| 4,611,054 | 9/1986 | Freidinger | 514/806 |
| 4,622,331 | 11/1986 | Jozic | 514/331 |
| 5,030,654 | 7/1991 | Barnish | 514/510 |
| 5,049,548 | 9/1991 | Greenlee | 514/18 |
| 5,051,405 | 9/1991 | Klein | 514/18 |

FOREIGN PATENT DOCUMENTS 478362  1/1992  European Pat. Off. .

OTHER PUBLICATIONS

Ruoslahti et al, "New Perspective in Cell Adhesion." Science 238 491–496 (1987).
Spatola et al, "Amide Bond Surrogate," Chem. Soc. J. Chem Communication 44(3) 821–833 (1988).

*Primary Examiner*—C. Warren Ivy
*Assistant Examiner*—Celia Chang
*Attorney, Agent, or Firm*—Richard S. Parr; Melvin Winokur; Paul Matukaitis

[57] ABSTRACT

Fibrinogen receptor antagonists of the formula:

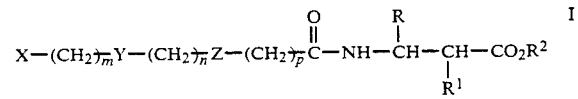

are disclosed for use in inhibiting the binding of fibrinogen to blood platelets and for inhibiting the aggregation of blood platelets.

9 Claims, No Drawings

FIBRINOGEN RECEPTOR ANTAGONISTS

CROSS-REFERENCE

This application is a continuation-in-part of U.S. Ser. No. 720,547, filed Jun. 25, 1991, now abandoned, which is a continuation-in-part of U.S. Ser. No. 696,904, filed May 7, 1991, now abandoned.

FIELD OF THE INVENTION

This invention relates to the discovery of fibrinogen receptor antagonists of Formula I for use in inhibiting the binding of fibrinogen to blood platelets and inhibiting the aggregation of blood platelets when administered to mammals, preferably humans.

BACKGROUND OF THE INVENTION

The interaction of platelets with the coagulation and fibrinolytic systems in the maintenance of hemostasis may become pathogenic, requiring prevention and treatment. The fibrinogen receptor antagonists of Formula I are useful in treating various diseases related to platelet aggregation and fibrin formation.

As interest in platelet inhibitors has reemerged as a result of a better understanding of the role of platelets and thrombosis in the pathogenesis of vascular disease, including unstable angina, acute myocardial infarction and stroke.

Platelets are cell-like anucleated fragments, found in the blood of all mammals, which participate in blood coagulation. Fibrinogen is a glycoprotein present as a normal component of blood plasma. Fibrinogen participates in platelet aggregation and fibrin formation in the blood clotting mechanism. Platelets are deposited at sites of vascular injury where multiple physiological agonists act to initiate platelet aggregation culminating in the formation of a platelet plug to minimize blood loss. If the platelet plug occurs in the lumen of a blood vessel, normal blood flow is impaired.

Platelet membrane receptors are essential in the process of platelet adhesion and aggregation. Interaction of fibrinogen with a receptor on the platelet membrane complex IIb/IIIa is known to be essential for normal platelet function.

Zimmerman et al., U.S. Pat. No. 4,683,291, describes peptides having utility in the study of fibrinogen-platelet, platelet-platelet, and cell-cell interactions. The peptides are described as having utility where it is desirable to retard or prevent formation of a thrombus or clot in the blood.

Pierschbacher et al., U.S. Pat. No. 4,589,881, describes the sequence of an 11.5 kDal polypeptide fragment of fibronectin which embodies the cell-attachment-promoting activity of fibronectin.

Ruoslahti et al., U.S. Pat. No. 4,614,517, describes tetrapeptides which alter cell-attachment activity of cells to various substrates.

Ruoslahti et al., U.S. Pat. No. 4,578,079, describes similar tetrapeptides having Ser substituted with Thr or Cys.

Pierschbacher et al., Proc. Natl. Acad. Sci., USA, Vol. 81, pp. 5985-5988, October, 1984, describe variants of the cell recognition site of fibronectin that retain attachment-promoting activity. Pierschbacher et. al. further assayed the cell attachment-promoting activities of a number of peptides, and found "that the arginine, glycine, and aspartate residues cannot be replaced even with closely related amino acids, but that several amino acids can replace serine without loss of activity."

Ruoslahti et al., Science, Vol. 238, pp. 491-497, Oct. 23, 1987, discuss cell adhesion proteins. They specifically state that "elucidation of the amino acid sequence of the cell-attachment domain in fibronectin and its duplication with synthetic peptides establish the sequence Arg-Gly-Asp (RGD) as the essential structure recognized by cells in fibronectin".

Cheresh, Proc. Natl. Acad. Sci. USA, Vol. 84, pp. 6471-6475, September, 1987, describes the Arg-Gly-Asp-directed adhesion receptor involved in attachment to fibrinogen and the von Willebrand Factor.

Adams et al., U.S. Pat. No. 4,857,508, describes tetrapeptides which inhibit platelet aggregation and the formation of a thrombus.

It is, therefore, an object of the present invention to provide fibrinogen receptor antagonists for use in inhibiting the binding of fibrinogen to blood platelets and inhibiting the aggregation of blood platelets. Another aspect of the present invention is to provide novel fibrinogen receptor antagonist compounds. Other objects of the present invention are to provide methods of inhibiting the binding of fibrinogen to blood platelets and inhibiting the aggregation of blood platelets, through the administration of novel fibrinogen receptor antagonist compounds. The above and other objects are accomplished by the present invention in the manner described below.

SUMMARY OF THE INVENTION

The present invention provides fibrinogen receptor antagonist compounds of the formula:

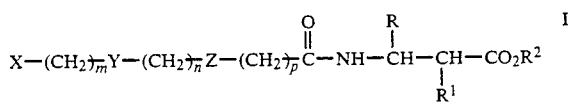

for use in inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of such compound is another feature of this invention.

DETAILED DESCRIPTION OF THE INVENTION

Fibrinogen receptor antagonist compounds of Formula I are useful in a method of inhibiting the binding of fibrinogen to blood platelets and for inhibiting the aggregation of blood platelets. Fibrinogen receptor antagonists of this invention are illustrated by compounds having the formula:

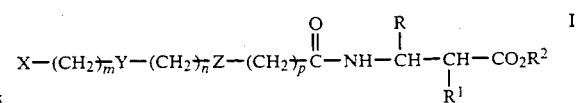

wherein:
X is

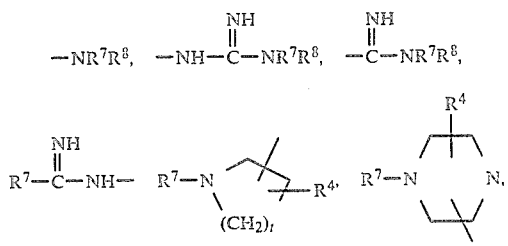

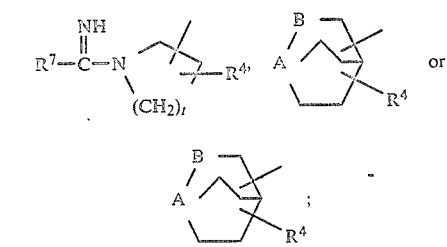

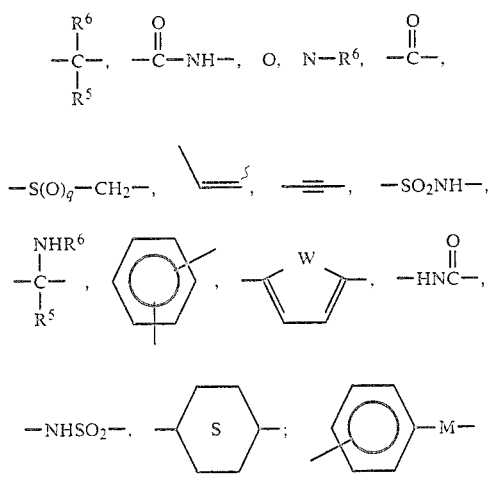

Where A=N and B=—CH$_2$—, or A=—CH— and B=NR$^7$;

Y is

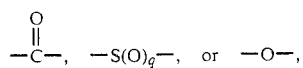

wherein M is $$-\overset{O}{\underset{\|}{C}}-, \quad -S(O)_q-, \quad \text{or} \quad -O-,$$

R and R$^1$ are independently hydrogen,
  aryl, wherein aryl is defined as a mono- or polycyclic aromatic system comprised of 5 or 6 membered rings containing 0, 1, 2, 3, or 4 heteroatoms selected from nitrogen, oxygen and sulfur, either unsubstituted or substituted, with one or more groups selected from hydroxyl, halogen, cyano, trifluromethyl, C$_{1-3}$alkoxy, C$_{1-5}$ alkylcarbonyloxy, C$_{1-5}$alkoxycarbonyl, C$_{1-5}$ alkyl, aminoC$_{1-5}$alkyl, hydroxycarbonylC$_{0-5}$ alkyl, or hydroxycarbonylC$_{1-5}$ alkoxy,
  C$_{0-6}$alkyl, either unsubstituted or substituted, with one or more groups selected from halogen, hydroxyl, C$_{1-5}$alkylcarbonylamino, arylC$_{1-5}$alkylcarbonylamino, aryloxy, C$_{1-10}$alkoxy, C$_{1-5}$alkoxycarbonyl, C$_{0-5}$alkylaminocarbonyl, C$_{1-5}$alkylcarbonyloxy, C$_{3-8}$ cycloalkyl, aryl, oxo, amino, C$_{1-6}$alkyl, C$_{1-3}$alkylamino, arylC$_{0-5}$alkylaminocarbonyl, phenylC$_{1-3}$alkylamino, aminocarbonylC$_{0-4}$alkyl, hydroxycarbonyl C$_{0-5}$alkyl, C$_{1-8}$alkylsulfonylamino, arylC$_{0-10}$alkylsulfonylamino, C$_{1-8}$alkylsulfonyl, arylC$_{0-10}$alkylsulfonyl, C$_{1-5}$alkyloxycarbonyl, amino, arylC$_{1-5}$alkyloxycarbonylamino, or arylC$_{1-10}$alkyloxy; provided that the carbon atom to which R or R$^1$ is attached bear only one heteroatom.

R$^2$ is
  hydrogen;
  C$_{1-12}$alkyl, unsubstituted of substituted with one or more C$_{1-6}$alkyl groups;

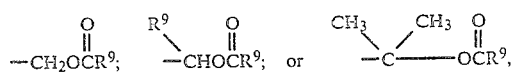

wherein R$^9$ is C$_{1-6}$alkyl branched or unbranched or phenyl, and wherein R$^9$, when appearing more than once, can be the same or different, R$^4$, R$^7$, and R$^8$ and are independently hydrogen,
  C$_{1-12}$alkyl, unsubstituted or substituted, with one or more C$_{1-6}$alkyl groups,
  arylC$_{0-4}$alkyl, or
  cyano provided that when R$^7$ and R$^8$ are independently cyano, X

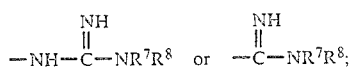

R$^5$ is
  hydrogen,
  C$_{0-6}$alkyl, either unsubstituted or substituted, with one or more groups selected from C$_{1-6}$ alkyl, C$_{1-5}$alkoxy, C$_{1-5}$alkoxycarbonyl, hydroxycarbonylC$_{0-4}$alkyl, aryl, aminoC$_{1-4}$alkyl, arylaminocarbonylC$_{0-4}$alkyl, C$_{1-4}$alkylsulfonyl, phenylC$_{0-4}$alkylsulfonyl, hydroxyl, or amino,
  hydroxycarbonyl,
  hydroxy or amino, provided that when R$^5$ is hydroxy or amino, R$^5$ is not attached to a carbon bearing a heteroatom;

R$^6$ is
  hydrogen,
  C$_{1-12}$alkyl, unsubstituted or substituted, with one or more C$_{1-6}$alkyl groups,
  arylC$_{0-3}$alkyl,
  C$_{1-4}$alkyloxycarbonyl,
  arylC$_{1-4}$alkyloxycarbonyl,
  C$_{1-4}$alkylaminocarbonyl, arylC$_{1-4}$alkylaminocarbonyl,
  C$_{2-5}$alkoxy,
  hydroxycarbonylC$_{2-5}$alkyl,
  aminocarbonylC$_{2-5}$alkyl;

m is 1-10;
n is 0-9;
q is 0-2;
t is 1-6;
p is 1 or 2;
W is O,

Z is

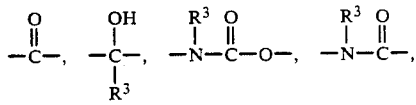

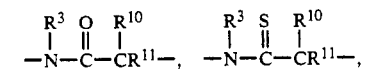

where $R^3$, when appearing in a structure more than once, can be the same or different, $R^3$ is hydrogen, aryl, wherein aryl is defined as a mono- or polycyclic aromatic system comprised of 5 or 6 membered rings containing 0, 1, 2, 3, or 4 heteroatoms selected from nitrogen, oxygen and sulfur, either unsubstituted or substituted, with one or more groups selected from hydroxyl, halogen, cyano, trifluromethyl, $C_{1-3}$alkoxy, $C_{1-5}$ alkylcarbonyloxy, $C_{1-5}$alkoxycarbonyl, $C_{1-5}$ alkyl, amino$C_{1-5}$alkyl, hydroxycarbonyl$C_{0-5}$ alkyl, or hydroxycarbonyl$C_{1-5}$alkoxy, $C_{0-6}$alkyl, either unsubstituted or substituted, with one or more groups selected from $C_{1-5}$alkoxycarbonyl, $C_{0-5}$ alkylaminocarbonyl, $C_{3-8}$cycloalkyl, aryl, $C_{1-6}$ alkyl, aryl$C_{0-5}$alkylaminocarbonyl, aminocarbonyl$C_{0-4}$alkyl, or hydroxycarbonyl $C_{0-5}$alkyl, hydroxy, alkoxy;

and $R^{10}$ and $R^{11}$ are, independently, as defined in R and $R^1$, or form a $C_{3-10}$ cycle;

or the pharmaceutically acceptable salts thereof, or optical isomers thereof.

In one embodiment of the present invention, the fibrinogen receptor antagonist has the following formula:

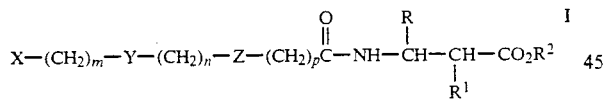

wherein:

X is

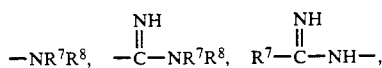

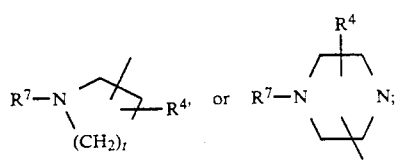

Y is

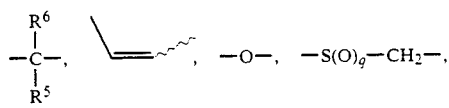

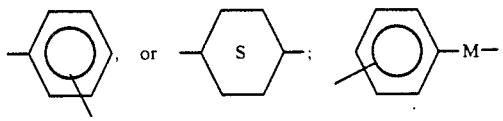

wherein M is

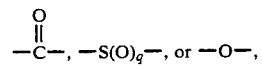

R and $R^1$ are independently chosen from phenyl, thiophene, imidazole, naphthyl, indole, indazole, thionaphthene, either unsubstituted or substituted, with hydroxy, halogen, hydroxycarbonyl $C_{0-5}$alkyl, $C_{1-3}$alkyl, either unsubstituted or substituted, with one or more groups selected from aryl, aryloxy, $C_{1-10}$alkoxy, $C_{0-5}$alkylaminocarbonyl, aryl$C_{0-5}$alkylaminocarbonyl, hydrogen, $C_{0-6}$alkyl, either unsubstituted or substituted, with one or more groups selected from halogen, hydroxyl, $C_{1-5}$alkylcarbonylamino, aryl$C_{1-5}$alkylcarbonylamino, aryloxy, $C_{1-10}$alkoxy, $C_{1-5}$alkoxycarbonyl, $C_{0-5}$alkylaminocarbonyl, $C_{1-5}$alkylcarbonyloxy, $C_{3-8}$cycloalkyl, aryl, oxo, amino, $C_{1-6}$alkyl, $C_{1-3}$alkylamino, aryl$C_{0-5}$alkylaminocarbonyl, phenyl$C_{1-3}$alkylamino, aminocarbonyl$C_{0-4}$alkyl, hydroxycarbonyl $C_{0-5}$alkyl, $C_{1-8}$alkylsulfonylamino, aryl$C_{0-10}$alkylsulfonylamino, $C_{1-8}$alkylsulfonyl, aryl$C_{0-10}$alkylsulfonyl, $C_{1-5}$alkyloxycarbonylamino, aryl$C_{1-5}$alkyloxycarbonylamino, or aryl$C_{1-10}$alkyloxy; provided that the carbon atom to which R or $R^1$ is attached bear only one heteroatom.

R2 is hydrogen;

$C_{1-12}$alkyl, unsubstituted or substituted with one or more $C_{1-6}$alkyl groups;

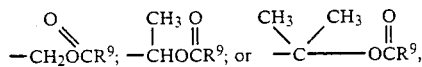

wherein $R^9$ is $C_{1-6}$alkyl branched or unbranched or phenyl, $R^4$, $R^7$, and $R^8$ are independently hydrogen, or $C_{0-3}$alkyl, unsubstituted or substituted, with one or more $C_{1-6}$alkyl groups;

$R^5$ is, hydrogen, $C_{0-3}$alkyl, either unsubstituted or substituted with one or more groups selected from amino, amino $C_{1-4}$alkyl, hydroxyl, arylaminocarbonyl $C_{0-4}$alkyl;

$R^6$ is, hydrogen, or hydroxycarbonyl$C_{2-4}$alkyl;

m is 1–5;

n is 0–4;

q is 0–2;

p is 1 or 2;

t is 1–3;

Z is

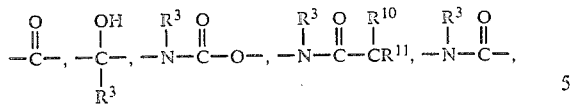

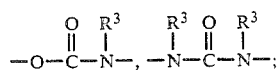

where $R^3$, when appearing more than once, can be the same or different, $R^3$ is hydrogen, aryl, wherein aryl is defined as a mono- or polycyclic aromatic system comprised of 5 or 6 membered rings containing 0, 1, 2, 3, or 4 heteroatoms selected from nitrogen, oxygen and sulfur, either unsubstituted or substituted, with one or more groups selected from hydroxyl, halogen, cyano, trifluromethyl, $C_{1-3}$alkoxy, $C_{1-5}$alkylcarbonyloxy, $C_{1-5}$alkoxycarbonyl, $C_{1-5}$alkyl, amino$C_{1-5}$alkyl, hydroxycarbonyl$C_{0-5}$ alkyl, or hydroxycarbonyl$C_{1-5}$alkoxy, $C_{0-6}$alkyl, either unsubstituted or substituted, with one or more groups selected from $C_{1-5}$alkoxycarbonyl, $C_{0-5}$alkylaminocarbonyl, $C_{3-8}$cycloalkyl, aryl, $C_{1-6}$alkyl, aryl$C_{0-5}$alkylaminocarbonyl, aminocarbonyl$C_{0-4}$alkyl, or hydroxycarbonyl $C_{0-5}$alkyl;

$R^{10}$ and $R^{11}$ are, independently, as defined in R and $R^1$, or form a $C_{3-10}$ cycle;

or the pharmaceutically acceptable salts thereof, or optical isomers thereof.

More preferred compounds of the invention have the following formula:

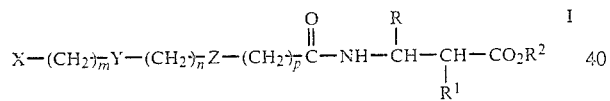

X is

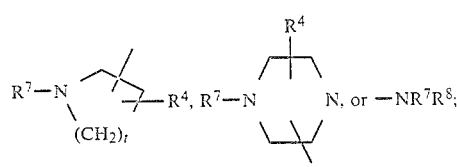

Y is

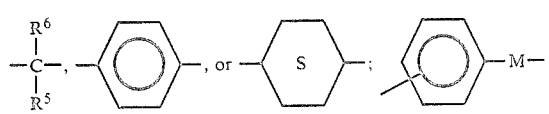

wherein M is

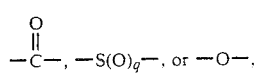

R and $R^1$ are independently chosen from phenyl, imidazole, indole, indazole, unsubstituted or substituted, with methyl, hydroxycarbonyl$C_{0-2}$ alkyl, hydrogen, $C_{1-6}$alkyl, either unsubstituted or substituted, with one or more groups selected from halogen, hydroxyl, $C_{1-5}$-alkylcarbonylamino, aryl$C_{1-5}$alkylcarbonylamino, aryloxy, $C_{1-10}$alkoxy, $C_{1-5}$alkoxycarbonyl, $C_{0-5}$alkylaminocarbonyl, $C_{1-5}$alkylcarbonyloxy, $C_{3-8}$cycloalkyl, aryl, oxo, amino, $C_{1-6}$alkyl, $C_{1-3}$alkylamino, aryl$C_{0-5}$alkylaminocarbonyl, phenyl$C_{1-3}$alkylamino, aminocarbonyl$C_{0-4}$alkyl, or hydroxycarbonyl $C_{0-5}$alkyl;

R2 is hydrogen;

$C_{1-12}$alkyl, unsubstituted of substituted with one or more $C_{1-6}$alkyl groups;

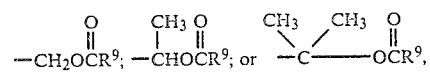

wherein $R^9$ is $C_{1-6}$alkyl branched or unbranched or phenyl, $R^4$, $R^7$, and $R^8$ are hydrogen;

$R^5$ is, hydrogen;

$R^6$ is, hydrogen;

m is 1-5;

n is 0-3;

p is 1 or 2 t is 2-4;

q is 0-2;

Z is

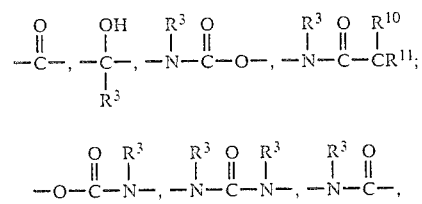

where $R^3$, when appearing more than once, can be the same or different, $R^3$ is hydrogen, $C_{1-12}$alkyl, unsubstituted or substituted, with one or more $C_{1-6}$alkyl groups, aryl, or aryl$C_{0-3}$alkyl, $R^{10}$ and $R^{11}$ are hydrogen, $C_{1-6}$alkyl, unsubstituted or substituted with one or more $C_{1-6}$alkyl groups, or aryl, or the pharmaceutically acceptable salts thereof, or optical isomers thereof;

Most preferred fibrinogen receptor antagonists are those of formula I wherein:

X is

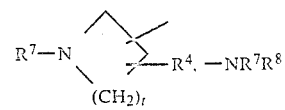

t = 3

Y is

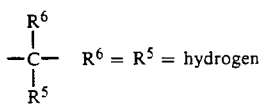

Z is

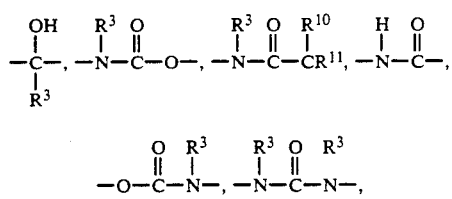

where $R^1$ = hydrogen

R is $C_{2-4}$alkyl, unsubstituted or substituted with one or more oxo, hydroxy, or aryl groups.

$R^2$ is hydrogen.

$R^{10}$ and $R^{11}$ = hydrogen $R^7$ and $R^8$ = hydrogen $R^3$ is hydrogen or $C_{1-4}$alkyl unsubstituted or substituted with one or more $C_{1-4}$alkyl or aryl groups.

The following compounds are especially preferred compounds of the invention:

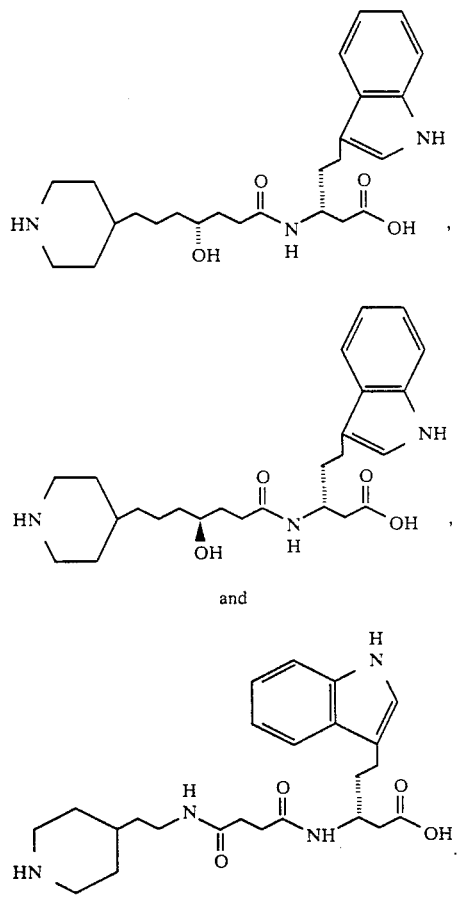

and

This invention includes the following abbreviation designations; Bn, benzyl; NMM, N-methylmorpholine; HOBt, 1-hydroxybenzotriazole; EDC, 1-(3-dimethylaminopropyl)-3-ethyl-carbodiimidehydrochloride; DMF, dimethylformamide; Pib, 4-(4-piperidyl)butan-oyl; pTSA, para toluenesulfonic acid; DMS, dimethylsulfide; TFA, trifluoroacetic acid; THF, tetrahydrofuran; DIBAL, diisobutylaluminum hydride; Boc, tert-butoxycarbonyl; Cbz, benzyloxycarbonyl; halogen, fluorine, chlorine, bromine, iodine; Suc, succinoyl; alpine borane, β-isopinocamphenyl-9-borabicyclo[3.3.1]-nonane TBDMS, tert-butyldimethylsilyl, Jones reagent, chromic acid.

The pharmaceutically acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I are useful in inhibiting the binding of fibrinogen to blood platelets, inhibiting aggregation of blood platelets, treatment of thrombus formation or embolus formation, and in the prevention of thrombus formation or embolus formation. These compounds are useful as pharmaceutical agents for mammals, especially for humans. The compounds of this invention may be administered to patients where prevention of thrombosis by inhibiting binding of fibrinogen to the platelet membrane glycoprotein complex IIb/IIIa receptor is desired. Compounds of this invention may also be used to prevent or modulate the progress of myocardial infarction, unstable angina and thrombotic stroke, in either acute or chronic settings. In addition, they may be useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb- /IIIa on the platelet membranes and fibrinogen adsorbed to the surface of the circuit. (Gluszko et al., *Amer. J. Physiol.*, 1987, 252: H, pp 615–621). Platelets released from artificial surfaces show impaired hemostatic function. Compounds of this invention may be administered to prevent adhesion.

Other applications of these compounds include prevention of platelet thrombosis, thromboembolism, reocclusion, and restenosis during and after thrombolytic therapy and prevention of platelet thrombosis, thromboembolism, reocclusion and restenosis after angioplasty of coronary and other arteries and after coronary artery bypass procedures.

The compounds of Formula I may be administered to mammals, preferably in combination with pharmaceutically-acceptable carriers or diluents, optionally with known adjuvants such as alum, in a pharmaceutical composition which is non-toxic and in a therapeutically effective amount, according to standard pharmaceutical practice. The compounds can be administered orally or parenterally, including intravenous, intramuscular, intraperitoneal, trans-dermal, subcutaneous and topical administration.

For oral use of a fibrinogen receptor antagonist according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment and prevention of diseases related to platelet aggregation, fibrin formation, and thrombus and embolus formation, comprising the administration of a therapeutically effective but non-toxic amount of the compounds of Formula I, with or without pharmaceutically acceptable carriers or diluents.

Compositions of this invention include fibrinogen receptor antagonist compounds of this invention in combination with pharmacologically acceptable carriers, e.g. saline, at a pH level e.g. 7.4, suitable for achieving inhibition of platelet aggregation. The compositions may also be combined with anticoagulants such as heparin or warfarin. The compositions may also be combined with thrombolytic agents such as plasminogen activators or streptokinase in order to inhibit platelet aggregation in more acute settings. The composition may further be combined with antiplatelet agents such as aspirin. The compositions are soluble in an aqueous medium, and may therefore be effectively administered in solution.

When a compound according to Formula I is used as a fibrinogen receptor antagonist in a human subject, the daily dosage will normally be determined by the prescribing physician with the dosage generally varying according to the age, weight, and response of the individual patient, as well as the severity of the patients symptoms.

In one exemplary application, a suitable amount of compound is administered orally to a heart attack victim subsequent to angioplasty. Administration occurs subsequent to angioplasty, and is in an amount sufficient to inhibit platelet aggregation, e.g. an amount which achieves a steady state plasma concentration of between about 0.01–50 $\mu$M preferably between about 0.01–10 $\mu$M.

The present invention also includes a pharmaceutical composition comprising compounds of the present invention in combination with tissue type plasminogen activator or streptokinase. The invention also includes a method for promoting thrombolysis and preventing reocclusion in a patient which comprises administering to the patient an effective amount of compositions of the invention.

The present invention provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amount of the compounds of this invention, with or without pharmaceutically acceptable carriers or diluents.

The present invention still further provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amounts of the compounds of this invention in combination with thrombolytic agents, such as tissue plasminogen activators or streptokinase, anticoagulants such as heparin or warfarin, or antiplatelet agents such as aspirin, with or without pharmaceutically acceptable carriers or diluents.

The novel indolylalkylamines of this invention are generally prepared from the appropriate indolylalkanol by initial protection of the alcohol with a trialkylsilyl or equivalent group followed by acylation of the indole nitrogen with an alkanoic anhydride. Deprotection of the alcohol with n-Bu$_4$NF in acetic acid followed by oxidation with oxalyl chloride/DMSO or other suitable oxidant provides the desired aldehyde which is olefinated under Wittig conditions with Ph$_3$P=CHCO$_2$C$_2$H$_5$ in a halocarbon solvent such as CH$_2$Cl$_2$ for 30 minutes to 6 hrs at 0°–60° C. Treatment of the resulting ester with S(−)-α-methylbenzylamine and separation of the resulting diastereomers gives chiral indolylamines such as 7.

The novel acids 18 of this invention are prepared by oxidation of N-Boc piperidine ethanol followed by Wittig reactions with Ph$_3$P=CHCO$_2$Et or similarly suitable reagent. Catalytic reduction over Pd/C followed by reduction with an appropriate metal hydride, such as Dibal, gives aldehyde 12. Condensation with the anion of ethyl propriolate, followed by sequential oxidation, with chromic acid or other suitable reagent, and reduction with a chiral Alpine borane gives the desired chiral alcohol 15. Silylation, catalytic reduction, de-esterification and coupling with amines such as 7 provides products 19. The final coupling reaction is carried out in solvents such as DMF or halocarbons such as CH$_2$Cl$_2$ by activating the acid with coupling reagents such as EDC or isobutyl chloroformate. The coupled products are de-protected if necessary by hydrolysis with alcoholic NaOH and subsequent HCl (gas) or TFA treatment.

Alternatively N-Boc piperidinethanol can be converted to its azide, via the iodide or other suitable halide. Catalytic reduction and treatment of the resulting amine with succinic anhydride provides acid 25. Coupling of this with 7 under normal amide coupling conditions followed by de-protection provides 28.

The compounds of Formula I are prepared according to the reaction schemes set forth below.

Compound 1, 3-indolepropanol, is available from Aldrich Chemical.

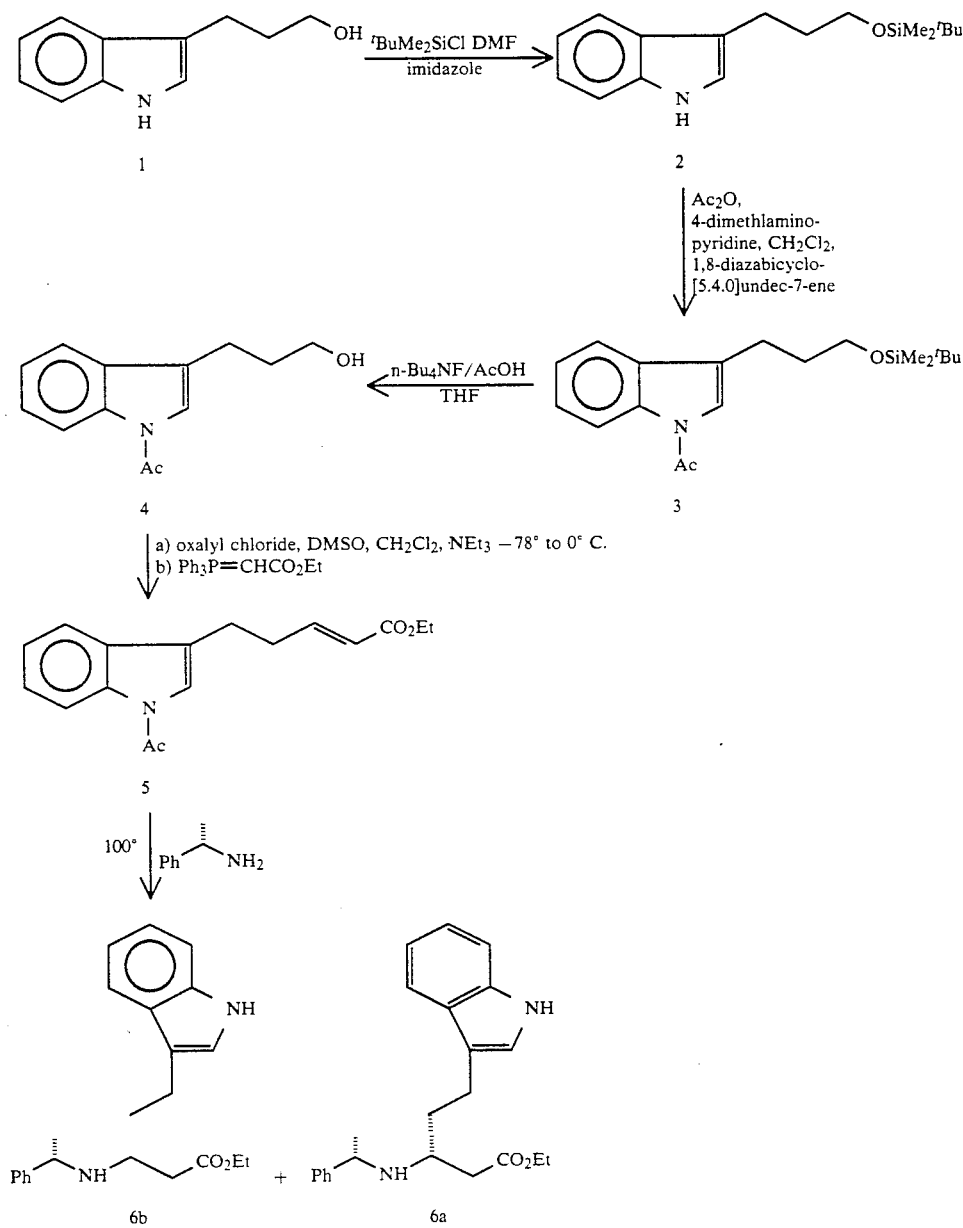

SCHEME 1

-continued
SCHEME 1
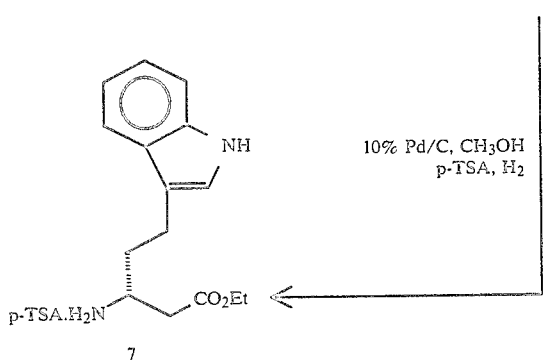
Compound 8, 2-piperidineethanol, is available from American Tokyo Kansei, Inc.
SCHEME 2
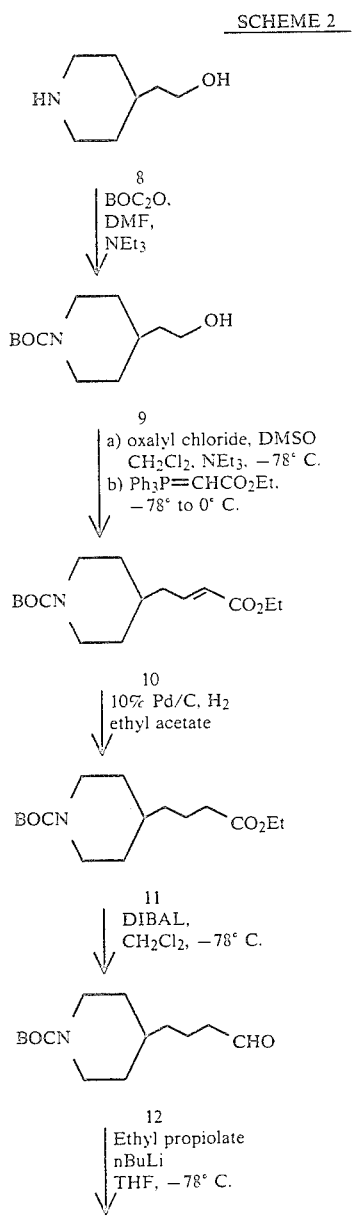
-continued
SCHEME 2
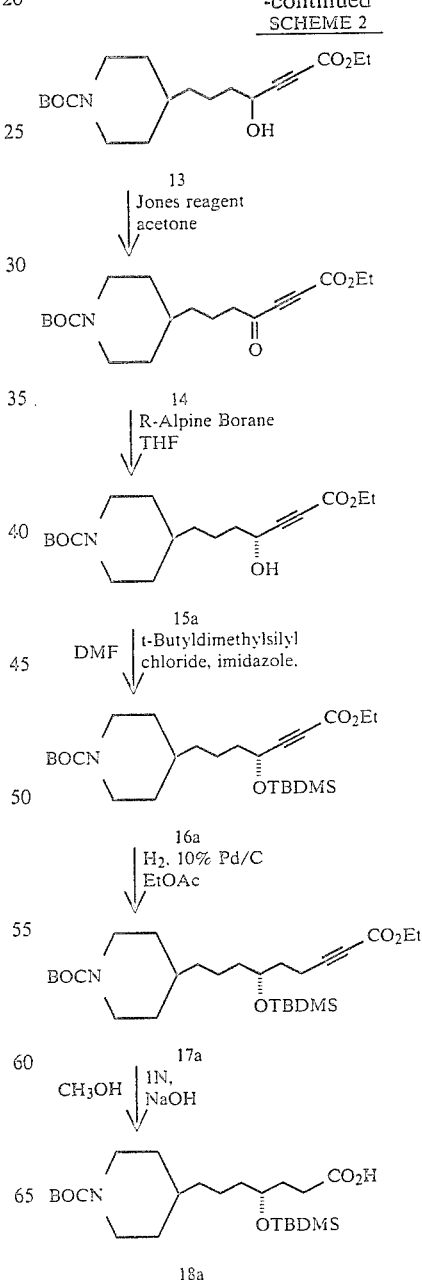

17
-continued
SCHEME 2
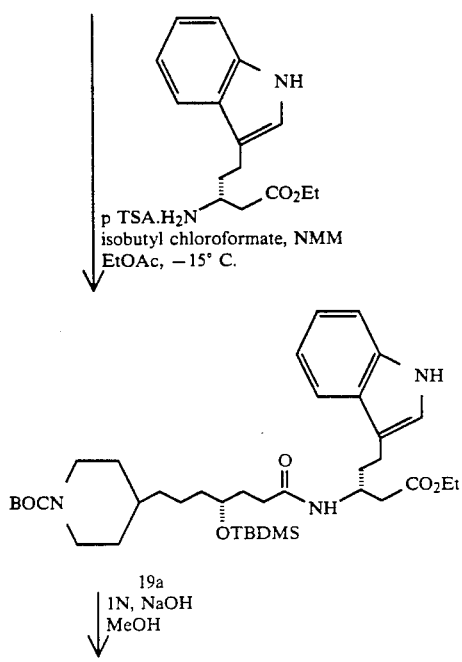
18
-continued
SCHEME 2
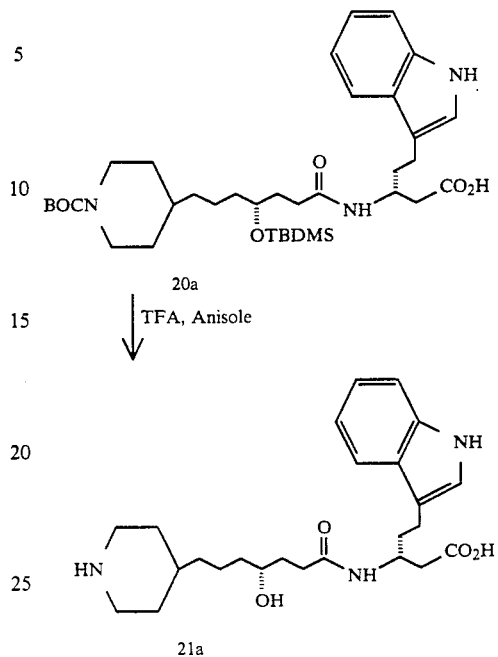
SCHEME 3
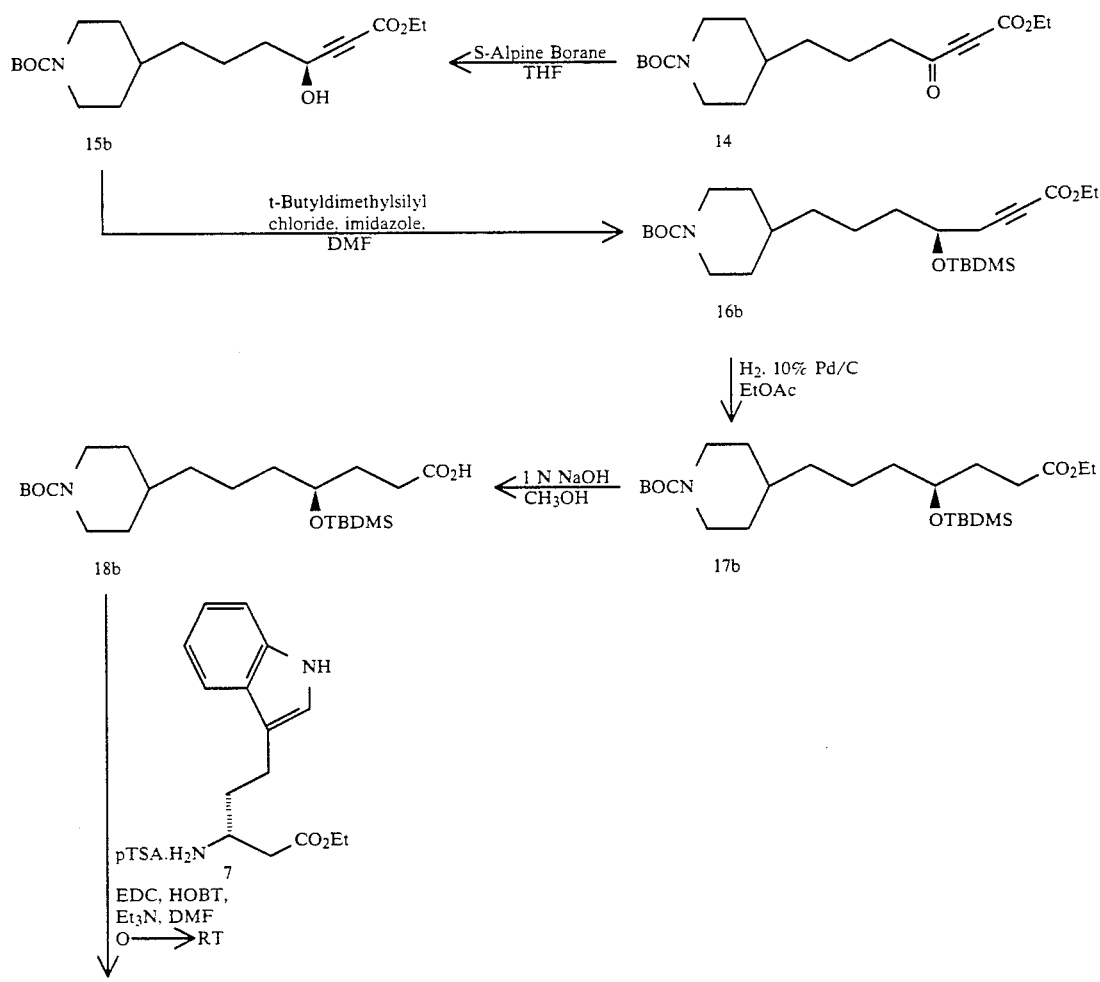

-continued
SCHEME 3
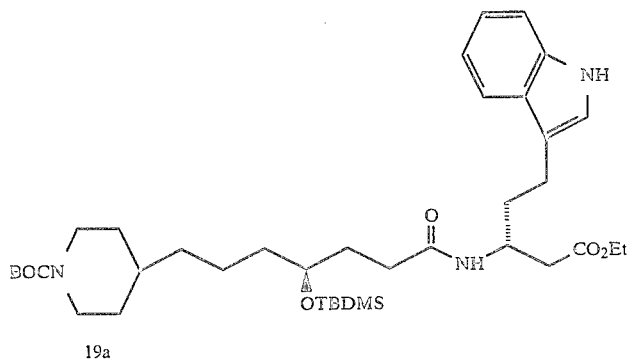
19a
1 N NaOH, MeOH ↓
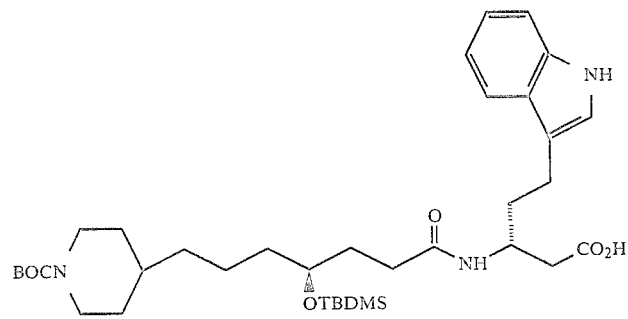
20b
TFA, Anisole ↓
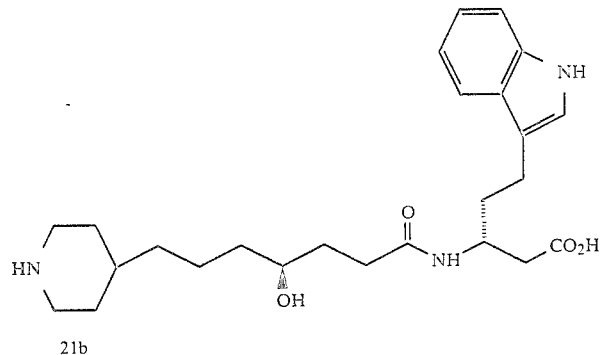
21b
SCHEME 4
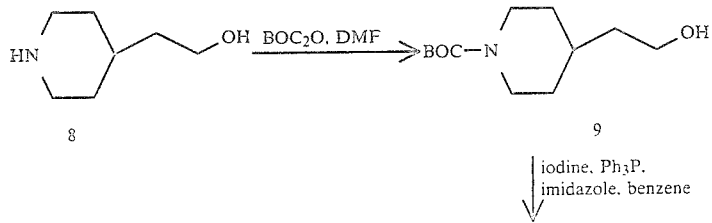
iodine, Ph₃P, imidazole, benzene ↓

SCHEME 4
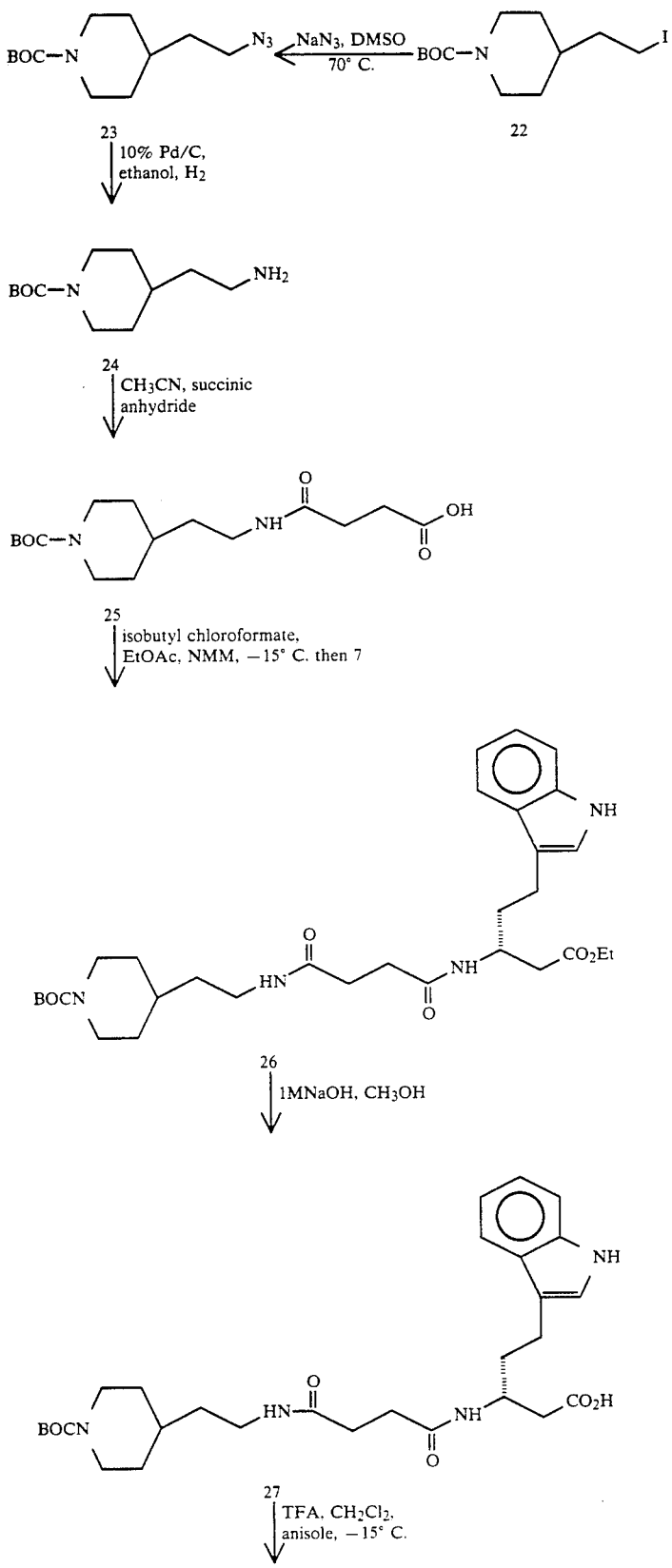

SCHEME 4

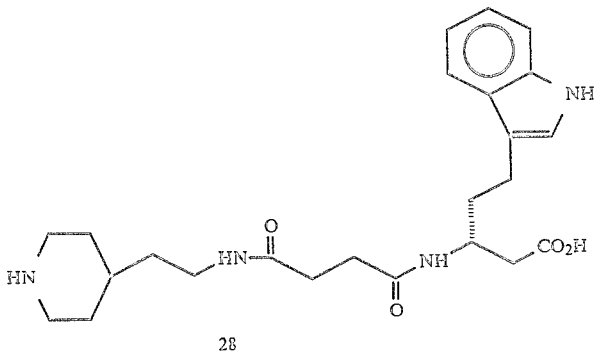

-continued

28

Preparation of
3-(Indol-3-yl)propanol-tert-butyldimethylsilyl ether (2)

To a stirring solution of 3-indolepropanol 1 (15 g, 86 mmol), DMF (200 mL), and imidazole (12.8 g, 0.19 mol) at 0° C. was added tert-butyldimethylsilyl chloride (14.2 g, 95 mmol) followed by removal of the cooling bath. After 20 hours the reaction mixture was diluted with ether and then washed with $H_2O$ (2 times) and brine, dried ($MgSO_4$), and concentrated to yield the silyl ether 2 (29 g) as an amber oil.

TLC Rf=0.54 (20% ethyl acetate/hexanes).

$^1$H NMR ($CDCl_3$) δ8.07 (bs, 1H), 7.77 (d, J=7 Hz, 1H), 7.49 (d, J=7 Hz, 1H), 7.33 (t, J=7 Hz, 1H), 7.26 (t, J=7 Hz, 1H), 7.12 (s, 1H), 3.84 (t, J=6 Hz, 2H), 2.95 (t, J=7 Hz, 2H), 2.08 (m, 2H), 1.08 (s, 9H), 0.25 (s, 3H), 0.22 (s, 3H).

Preparation of
N-Acetyl-3-(indol-3-yl)propanol-tert-butyldimethylsilyl ether (3)

A solution of the indole 2 (29 g, 86 mmol), $CH_2Cl_2$ (450 mL), 1,8-diazobicyclo[5.4.0]undec-7-ene (38 mL, 0.26 mol), 4-dimethylaminopyridine (1.0 g, 8.5 mmol), and acetic anhydride (32 mL, 0.34 mol) was stirred for 1 week at ambient temperature. The reaction mixture was concentrated and then diluted with ether. The ether was then washed with $H_2O$, 5% $KHSO_4$ and brine, dried ($MgSO_4$), and concentrated. Flash chromatography (silica, 5% ethyl acetate/hexanes) gave the acylated product 3 (27 g) as a yellow oil.

TLC Rf=0.56 (20% ethyl acetate/hexanes).

Preparation of N-Acetyl-3-(indol-3-yl)propanol (4)

To a stirred solution of the silyl ether 3 (27 g, 81 mmol) in THF (270 mL) at ambient temperature was added a premixed solution of n-$Bu_4$NF (1M in THF: 244 mL, 0.24 mol) and AcOH (14 mL, 0.24 mmol) (1:1). After 20 hours the reaction mixture was diluted with ether and then washed with $H_2O$ (2 times) and brine, dried ($MgSO_4$), and concentrated to give the alcohol 4 (19 g) as a yellow crystalline solid. TLC Rf=0.35 (60% ethyl acetate/hexanes);

$^1$H NMR ($CDCl_3$) δ8.42 (m, 1H), 7.55 (d, J=7 Hz, 1H), 7.36 (t, J=7 Hz, 1H), 7.29 (t, J=7 Hz, 1H), 7.27 (7d, J=7 Hz, 1H), 7.22 (s, 1H), 3.76 (t, J=7 Hz, 2H), 2.82 (t, J=7 Hz, 2H) 2.61 (s, 3H), 2.00 (m, 2H).

Preparation of 5-(N-Acetylindol-3-yl)pent-2-enoic acid ethyl ester (5)

To a stirring solution of oxalyl chloride (11.4 mL, 0.13 mol) in $CH_2Cl_2$ (440 mL) at −78° C. was added dry DMSO (2.4 mL, 0.17 mol) dropwise. After 5 minutes, gas evolution ceased and the alcohol 4 (19 g, 87 mmol) in $CH_2Cl_2$ (40 mL) was added. After 30 minutes, $NEt_3$ (73 mL, 0.52 mol) was added to effect a thick slurry. The cooling bath was removed and the reaction stirred for an additional 15 minutes before adding (carbethoxymethylene)triphenyl phosphorane (33.5 g, 96 mmol). After 2.0 hours, the reaction mixture was diluted with ether and then washed with $H_2O$ (2 times), 5% $KHSO_4$ and brine, dried ($MgSO_4$), and concentrated. Flash chromatography (20% ethyl acetate/hexanes) gave the olefin 5 (14 g) as a white solid.

TLC Rf=0.54 (60% ethyl acetate/hexanes).

$^1$H NMR ($CDCl_3$) 8.42 (bd, 1H), 7.50 (d, J=7 Hz, 1H), 7.34 (t, J=7 Hz, 1H), 7.28 (t, J=7 Hz, 1H), 7.19 (bs, 1H), 7.03 (dt, J=18 and 7 Hz, 1H), 5.88 (d, J=18 Hz, 1H), 4.19 (q, J=7 Hz, 2H), 2.87 (t, J=7 Hz, 2H), 2.63 (m, 2H), 2.61 (s, 3H), 1.28 (t, J=7 Hz, 3H).

Preparation of
N-(S)-α-Methylbenzyl-3-(S)-[2-(indol-3-)ethyl]β-alanine ethyl ester (6b) and N-(S)-α-Methylbenzyl-3-(R)-[2-(indol-3-yl)ethyl]β-alanine ethyl ester (6a)

A mixture of olefin 5 (1.00 g, 3.5 mmol) and S-(−)-α-methylbenzylamine (1.8 mL, 14 mmol) was heated under a cold finger at 100° C. for 64 hours. The cooled reaction mixture was applied directly to a flash chromatography column (silica, 20% ethyl acetate/hexanes). The (S,S) isomer (6b) eluted first (396 mg, 28%) as a viscous yellow oil. The (S,R) isomer (6a) eluted next (484 mg, 34%) as a viscous yellow oil. 6b: Rf0.52 (60% EtOAc/hexanes);

$^1$H NMR (400 MHz, $CDCl_3$) δ7.84 (br s, 1H), 7.52 (dd, J=7.9, 0.7 Hz, 1H), 7.20–7.35 (m, 6H), 7.16 (tm, J=7.1, 1.3 Hz, 1H), 7.08 (tm, J=7.3, 1.1 Hz, 1H), 6.70 (br d, J=2.4 Hz, 1H), 4.10 (q, J=7.1 Hz, 2H), 3.90 (q, J=6.6. Hz, 1H), 2.80–2.90 (m, 2H), 2.68 (ABX dt, J=16, 7.9 Hz, 1H), 2.53 (ABX dd, J=14.5, 5.9 Hz, 1H), 2.42 (ABX dd, J=14.6, 5.3 Hz, 1H), 1.79 (q, J=7.5 Hz, 2H), 1.33 (d, J=6.4 Hz, 3H). 1.22 (t, J=7.1 Hz, 3H): [α]$_D$−30.3° (c=0.0148 g/mL, $CHCl_3$) 6a: Rf0.42 (60% EtOAc/hexanes). $^1$H NMR (400 MHz, $CDCl_3$) δ7.95 (br s, 1H), 7.57 (dd, J=7.5, 0.7 Hz, 1H), 7.34 (dm, J=8.1, 0.7 Hz, 1H), 7.17–7.30 (m, 1H), 7.11 (tm, J=7.9, 0.9 Hz, 1H), 6.89 (br d, J=2.2 Hz, 1H), 4.02–4.15 (ABX m, 2H), 3.89 (q, J=6.6 Hz, 1H), 2.95 (m, 1H), 2.82 (ABX ddd, J=15, 9.7, 5.9 Hz, 1H), 2.69 (ABX ddd, J=15, 9.7, 60 Hz, 1H), 2.47 (ABX dd, J=15.0, 5.1 Hz, 1H), 2.40

(ABX dd, J=15.0, 7.7 Hz, 1H), 1.96 (m, 1H), 1.83 (m, 1H), 1.30 (d, J=6.6 Hz, 3H), 1.21 (td, J=7.1, 0.7 Hz, 3H); [α]$_D$−53.7° (c=0.01185 g/mL, CHCl$_3$).

Preparation of (R)-3-(2-(indol-3-yl)ethyl)β-alanine ethyl ester-pTSA salt (7)

To a solution of 6a (1.0 g, 2.5 mmol) in 13 mL methanol was added p-TSA (0.485 g, 2.5 mmol) and 10% Pd/C (0.20 g). The mixture was stirred under a balloon of hydrogen overnight, then filtered through a pad of celite and concentrated to yield 7 (1.49 g) as a tan, foamy solid.

$^1$H NMR (300 MHz, CDCl$_3$) δ8.26 (br s, 2H), 7.79 (d, J=8.1 Hz, 2H), 7.43 (d, J=7.6 Hz, 1H), 7.37 (d, J=8.1 Hz, 1H), 7.33-7.08 (m), 6.83 (br s, 1H), 4.25 (br m, 1H), 4.07 (q, J=7.1 Hz, 2H), 3.16-3.06 (m), 2.85-2.73 (m, 2H), 2.51 (dt, J=15, 7.8 Hz, 1H), 2.35 (s, 3H), 2.28 (m, 1H), 1.71 (d, J=6.6 Hz, 2H), 1.18 (t, J=7.1 Hz, 3H).

Preparation of N-BOC-4-piperidineethanol (9)

To a stirred solution of 4-piperidineethanol 8 (18.7 g. 0.14 mol) and DMF (200 mL) at 0° C. was added N-tert-butoxycarbonyl anhydride (31 g, 0.14 mol). After 1 hour the cooling bath was removed and the reaction mixture stirred for 20 hours. The reaction mixture was diluted with ether and then washed with water (2×) and brine, dried (MgSO$_4$), and concentrated to furnish 9 (26 g, 62%) as a colorless oil.

TLC R$_f$=0.25 (40% ethyl acetate/hexanes).

$^1$H NMR (300 MHz, CDCl$_3$) δ4.09 (bs, 2H), 3.72 (t, J=7 Hz, 2H), 2.70 (m, 2H), 1.75-1.10 (m, 7H), 1.46 (s, 9H).

Preparation of Ethyl 4-(N-BOC-4-piperidyl)trans-crotonate (10)

To a stirred solution of oxalyl chloride (0.43 mL, 5.0 mmol) in CH$_2$Cl$_2$ (20 mL) at −78° C. was added DMSO (0.52 ml, 7.0 mmol) dropwise. After gas evolution subsided (~5 minutes) the alcohol 9 (0.8 g, 3.5 mmol) in CH$_2$Cl$_2$ (20 mL) was added in a stream. After 20 minutes triethylamine (1.7 mL, 12 mmol) was added dropwise and then the cooling bath removed. After 20 minutes (carbethoxymethylene) triphenylphosphorane (1.4 g, 4.0 mmol) was added. After 2.0 hours the reaction mixture was diluted with petroleum ether and then washed sequentially with H$_2$O, 5% KHSO$_4$, and brine, dried (MgSO$_4$), and concentrated. Flash chromatography (silica, 15% ethyl acetate/hexanes) gave the ester 10 (0.57 g) as a colorless oil.

TLC Rf=0.79 (50% ethyl acetate/hexanes).

$^1$H NMR (CDCl$_3$) δ6.91 (dt, J=16 and 7 Hz, 1H), 5.81 (bd, J=17 Hz, 1H), 4.18 (q, J=7 Hz, 2H), 4.08 (m, 2H), 2.67 (m, 2H), 2.14 (t, J=7 Hz, 2H), 1.70-1.05 (m, 5H), 1.44 (S,9H), 1.28 (t, J=7H, 3H).

Preparation of Ethyl 4-(N-BOC-4-piperidyl) butyrate (11)

The olefin 10 (26 g, 87 mmol) in ethyl acetate (500 mL) was hydrogenated, at ambient temperature, under a hydrogen atmosphere (1 atm) in the presence of 10% Pd/C (5.0 g) overnight. The reaction mixture was then purged with argon followed by filtration through a celite pad. Concentration of the filtrate followed by flash chromatography (silica, 10% ethyl acetate/hexanes) gave the ester 11 (24 g) as a crystalline solid.

TLC R$_f$=0.52 (20% ethyl acetate/hexanes).

$^1$H NMR (CDCl$_3$) δ4.16 (q, J=7 Hz, 2H), 4.10 (m, 2H), 2.69 (m, 2H), 2.31 (t, J=7 Hz, 2H), 1.68 (m, 4H), 1.38 (s, 9H), 1.40 (m, 1H), 1.11 (m, 2H).

Preparation of 4-(N-BOC-4-piperidyl)butanal (12)

DIBAL (1.5M in toluene, 17.5 mL, 26 mmol) was added dropwise to a solution of ester 11 (3.0, 10.5 mmol) in 53 mL dry dichloromethane at −78° C. After 2.5 hours an additional quantity of DIBAL (7.0 mL, 10.5 mmol) was added. Thirty minutes later the reaction was quenched at −78° C. by the addition of 150 mL of 5% aqueous ethyl acetate. After 20 minutes the cloudy mixture was warmed to RT, washed with 250 mL saturated potassium sodium tartrate, then the organic layer was washed with water, fresh saturated potassium sodium tartrate, water, and brine. After drying (MgSO$_4$) and concentration, chromatography (silica, 15% EtOAc/hexane) provided aldehyde 12 (1.97 g, 73%) as a clear colorless oil. R$_f$0.45 (40% ethyl acetate/hexane):

$^1$H NMR (300 MHz, CDCl$_3$) δ9.78 (t, J=1.7 Hz, 1H), 4.09 (br d. J=13 Hz, 2H), 2.68 (td, J=13.0, 2.1 Hz, 2H), 2.45 (td, J=7.3, 1.7 Hz, 2H), 1.72-1.51 (m, 4H), 1.46 (s, 9H), 1.40-1.24 (m, 3H), 1.05 (qd, J=12.0, 3.4 Hz, 2H).

Preparation of Ethyl [7-(N-BOC-4-piperidyl)-4-hydroxy]hept-2-ynoate (13)

n-Butyllithium (1.6M in hexanes 24 mL, 38.5 mmol) was added to a solution of ethyl propiolate (3.91 mL, 38.5 mmol) in dry THF at −78° C. After 20 minutes a solution of aldehyde 12 (1.97 g, 7.71 mmol) in 8 mL dry THF was added and the clear yellow solution was stirred for 1 hour. The reaction was quenched by the addition of 7.2 mmol acetic acid, warmed to RT, diluted with ether and washed with saturated NaHCO$_3$ until basic, then by brine. The dried (MgSO$_4$) concentrate was purified by flash chromatography (silica, 30% ethyl acetate/hexane) providing racemic alcohol 13 (2.19 g, 80%) as a yellow oil.

R$_f$0.35 (30% ethyl acetate/hexane).

$^1$H NMR (300 MHz, CDCl$_3$) δ4.51 (q, J=5.9 Hz, 1H), 4.26 (q, J=7.1 Hz, 2H), 4.1 (br s, 2H), 2.68 (br t, J=12 Hz, 2H), 2.13 (d, J=5.8 Hz, 1H), 1.82-1.60 (m), 1.60-1.25 (m), 1.47 (s, 9H), 1.34 (t, J=7.1 Hz, 3H), 1.09 (qd, J=12.3, 45 Hz, 2H).

Preparation of Ethyl [7-(N-BOC-4-piperidyl)-4-oxo]-hept-2-ynoate (14)

Alcohol 13 (4.41 g, 12.4 mmol) was dissolved in 62 mL acetone and cooled to −10° C. Jones reagent (Chromic acid, 4.5 mL) was added portionwise during 50 minutes, then the reaction was allowed to proceed for 40 minutes more. The brown mixture was diluted with 200 mL ether, washed twice with water, then with 5% KHSO$_4$, sat. NaHCO$_3$, and brine, dried (MgSO$_4$), and concentrated. Flash chromatography (silica, 15% ethyl acetate/hexane) provided ketone 14 (2.72 g, 62%) as a light yellow oil, R$_f$ 0.51 (30% ethyl acetate/hexane):

$^1$H NMR (300 MHz, CDCl$_3$) δ4.34 (q, J=7.1 Hz, 2H), 4.1 (br s, 2H), 2.7 (m, 2H), 2.66 (t, J=7.3 Hz, 2H), 1.80-1.65 (m, 4H), 1.48 (s, 9H), 1.45-1.25 (m), 1.39 (t, J=7.1 Hz, 3H), 1.13 (qd, J=12, 4.2 Hz, 2H).

Preparation of Ethyl [7-(N-BOC-4-piperidyl)-4(R)-hydroxy]hept-2-ynoate (15a)

A solution of R-Alpine-Borane ® (0.5M in THF, 7.5 mL, 3.8 mmol) was added dropwise to neat ketone 14

(0.66 g, 1.8 mmol) at 0°, then warmed to RT. After 2 days acetaldehyde (0.4 mL, 7.2 mmol) was added and allowed to react for 15 minutes before removing the solvent. The resulting mixture was diluted with 10 mL ether, cooled to 0°, ethanolamine (0.25 g, 4.1 mmol) was added, and after 15 minutes the resulting white ppt was removed by filtration. The filtrate was washed with brine, dried (MgSO$_4$), and concentrated, followed by chromatography (silica, 20% ethyl acetate/hexane) provided R alcohol 15a (0.53 g, 79%) as a colorless oil, R$_f$ 0.35 (30% ethyl acetate/hexane):

$^1$H NMR (300 MHz, CDCl$_3$) δ4.51 (q, J=5.9 Hz, 1H), 4.26 (q, J=7.1 Hz, 2H), 4.1 (br s, 2H), 2.68 (br t, J=12 Hz, 2H), 2.13 (d, J=5.8 Hz, 1H), 1.82–1.60 (m), 1.60–1.25 (m), 1.47 (s, 9H), 1.34 (t, J=7.1 Hz, 3H), 1.09 (qd, J=12.3, 4.5 Hz, 2H): e.e., 76%.

Preparation of Ethyl
[7-(N-BOC-4-piperidyl)-4(R)-(t-butyldimethylsilyloxy)]hept-2-ynoate (16a)

A solution of alcohol 15a (0.500 g, 1.41 mmol) in 7 mL DMF was treated with imidazole (0.251 g, 3.68 mmol) and t-butyldimethylsilyl chloride (0.278 g, 1.84 mmol). After 3 days the mixture was diluted with ether and washed with 1% HCl, the aqueous layer re-extracted with ether, and the combined organic extracts were washed with 1% HCl, sat. NaHCO$_3$, and brine, dried (MgSO$_4$), and concentrated. Flash chromatography (silica, 7.5% ethyl acetate/hexane) provided R silyl ether 16a (0.340 g, 51%) as a colorless oil. R$_f$ 0.74 (30% ethyl acetate/hexane): $^1$H NMR (300 MHz, CDCl$_3$) δ4.47 (t, J=6.2 Hz, 1H), 4.25 (q, J=7.2 Hz, 2H), 4.1 (br s, 2H), 2.68 (br t, J=12 Hz, 2H), 1.8–1.6 (m, 2H), 1.55–1.25 (m), 1.47 (s, 9H), 1.33 (t, J=7.2 Hz, 3H), 1.08 (qd, J=12.5, 4.0 Hz, 2H), 0.92 (s, 9H), 0.17 (s, 3H), 0.13 (s, 3H).

Preparation of Ethyl
[7-(N-BOC-4-piperidyl)-4(R)-(t-butyldimethylsilyloxy)]heptanoate (17a)

A mixture of alkyne 16a (0.340 g, 0.726 mmol) and 10% Pd/C (68 mg) in 5 mL ethyl acetate was held under 1 atm hydrogen for 2 hours, then filtered through a Celite pad. Concentration provided 17a (328 mg, 96%) as a colorless oil, R$_f$ 0.39 (10% ethyl acetate/hexane): $^1$H NMR (300 MHz, CDCl$_3$) δ4.15 (q, J=7.1 Hz, 2H), 4.1 (br, 2H), 3.72 (qn, J=6.2 Hz, 1H), 2.69 (br t, J=12.5 Hz, 2H), 2.68 (t, J=8.0 Hz, 2H), 1.90–1.65 (m, 4H), 1.48 (s, 9H), 1.5–1.2 (m), 1.28 (t, J=7.1 Hz, 3H), 1.09 (qd, J=12.4, 3.9 Hz, 2H), 0.91 (s, 9H), 0.069 (s, 3H), 0.065 (s, 3H).

Preparation of Ethyl
[7-(N-BOC-4-piperidyl)-4(R)-(t-butyldimethylsilyloxy)]heptanoate (18a)

Sodium hydroxide (1N, 1.01 mL, 1.01 mmol) was added to a solution of ester 17a (318 mg, 0.68 mmol) in 5 mL methanol. After 3 hours additional NaOH (1N, 0.5 mL, 0.5 mmol) was added, then again at 5 hours (1N, 0.5 mL, 0.5 mmol). After stirring over night the yellow solution was concentrated and the residue was diluted with water and washed with ether. The aqueous phase was acidified with 5% KHSO$_4$, extracted twice with ethyl acetate, and the combined extracts were washed with brine before drying (MgSO$_4$) and concentration to yield acid 18a (280 mg, 94%) as a colorless oil, R$_f$ 0.72 (ethyl acetate):

$^1$H NMR (300 MHz, CDCl$_3$) δ4.1 (br, 2H), 3.741 (qn, J=6.0 Hz, 1H), 2.67 (br t, J=12 Hz, 2H), 2.44 (t, J=8.2 Hz, 2H), 1.8–1.6 (m, 4H), 1.48 (s, 9H), 1.5–1.2 (m), 1.08 (qd, J=13.4 Hz, 2H), 0.91 (s, 9H), 0.070 (s, 3H), 0.067 (s, 3H).

Preparation of
[7-(N-BOC-4-piperidyl)-4(R)-(t-butyldimethylsilyloxy)]heptanoyl-[3(R)-[2-(indol-3-yl)ethyl]β-alanine ethyl ester (19a)

Isobutyl chloroformate (22 μL, 0.17 mmol) was added to a solution of acid 18a (76 mg, 0.17 mmol) and N-methylmorpholine (19 μL, 0.17 mmol) in 1 mL ethyl acetate at −15°. After 30 minutes amine salt 7 (89 mg, 0.20 mmol) and N-methylmorpholine (57 μL, 0.51 mmol) were added. Three hours later 0.2 mL DMF was added to make the mixture homogeneous, then after one hour additional 7 (37 mg, 0.085 mmol) was added. Following an additional 30 minutes reaction the mixture was diluted with ethyl acetate, washed with water, 5% KHSO$_4$, sat NaHCO$_3$, and brine, dried (MgSO$_4$), and concentrated. Flash chromatography (silica, 20–30% ethyl acetate/hexane) provided amide 19a (43 mg, 36%) as a clear, light yellow oil, R$_f$ 0.54 (50% ethyl acetate/hexane):

$^1$H NMR (300 MHz, CDCl$_3$) δ8.20 (br s, 1H), 7.58 (d, J=7.8 Hz, 1H), 7.37 (d, J=7.9 Hz, 1H), 7.02 (td, J=8.0, 1.0 Hz, 1H), 7.12 (td, J=7.9, 1.1 Hz, 1H), 7.06 (d, J=2.2 Hz, 1H), 6.17 (d, J=9.0 Hz, 1H), 4.40 (apparent oct. J=4 Hz, 1H), 4.15 (q, J=7.1 Hz, 2H), 4.05 (m, 2H) 3.72 (qn, J=6.0 Hz, 1H), 2.82 (q, J=8.0 Hz, 2H), 2.67 (br t, J=12 Hz, 2H), 2.58 (dd, J=5.1, 2.0 Hz, 2H), 2.23 (m, 2H), 2.1–1.6 (m, 6H), 1.48 (s, 9H), 1.45–1.2 (m), 1.26 (t, J=7.1 Hz, 3H), 1.04 (m, 2H), 0.91 (s, 9H), 0.072 (s, 3H), 0.065 (s, 3H).

Preparation of
[7-(N-BOC-4-piperidyl)-4(R)-(t-butyldimethylsilyloxy)]heptanoyl-[3(R)-[2-(indol-3-yl)ethyl]β-alanine (20a)

Ester 19a (43 mg, 62 μmol) was dissolved in 0.4 mL methanol, and NaOH (1N, 124 μL, 124 μmol) was added. After stirring over night additional NaOH (1N, 31 μL, 31 mmol) was added and the hydrolysis was continued for 24 hours more. Solvent was removed and the residue was taken up in water and ethyl acetate. The pH was adjusted to 1 with 5% KHSO$_4$ and the organic phase was washed with 5% KHSO$_4$ then brine, dried (MgSO$_4$) and concentrated providing the acid 20a (44 mg) as a yellow oil.

$^1$H NMR (300 MHz, CDCl$_3$) δ8.21 (br s, 1H), 7.64 (d, J=7.9 Hz, 1H), 7.43 (d, J=8.1 Hz, 1H), 7.26 (td, J=7.1, 1.5 Hz, 1H), 7.18 (td, J=8.0, 1.2 Hz, 1H), 7.10 (d, J=2.3 Hz, 1H). 6.27 (d, J=4.4, m Hz, 1H). 4.1 (br 2), 3.76 (br m, 1H), 2.88 (m, 2H), 2.8–2.6 (m, 4H), 2.35–2.0 (m), 1.9–1.6 (m), 1.53 (s, 9H), 1.5–1.3 (m), 1.1 (m, 2H), 0.96 (s, 9H), 0.123 (s, 3H), 0.119 (s, 3H).

Preparation of
[7-(4-piperidyl)-4(R)-hydroxy]heptanoyl-[3(R)-[2-(indol-3-yl)ethyl]β-alanine (21a)

Acid 20a (44 mg, 67 μmol) was dissolved in 0.5 mL methylene chloride along with anisole (15 μL, 130 μmol) and cooled to −15°. TFA (168 μL) was added and after 20 minutes the solvents were removed and the residue was azeotroped with toluene. Flash chromatography (silica, 10:0.9:0.9. EtOH:conc. NH$_4$OH:water) and preparative HPLC (C-18, water/acetonitrile/TFA) and flash chromatography again (silica, 10:0.9:0.9, EtOH:conc NH4OH:water) provided 21a (10 mg, 34% for 2 steps), $R_f$ 0.23 (10:1:1 EtOH:conc NH4OH:H2O):

$^1$H NMR (400 MHz, D2O) δ 7.56 (d, J=7.5 Hz, 1H), 7.41 (d, J=8.1 Hz, 1H), 7.15 (t, J=7.1 Hz, 1H), 7.09 (s, 1H), 7.06 (t, J=7.1 Hz, 1H), 4.16 (m, 1H), 3.51 (m, 1H), 3.19 (br d, J=12 Hz, 2H), 2.75-2.65 (m, 4H), 2.54 (ABX dd, J=15.4, 5.7 Hz, 1H), 2.43 (ABX dd, J=15.4, 8.0 Hz, 1H), 2.18-2.10 (m, 2H), 1.92-1.92-1.81 (m, 2H), 1.69-1.57 (m, 4H), 1.37-1.26 (m, 4H), 1.20-1.05 (m, 4H); d.e., 90%.

Preparation of Ethyl [7-(N-BOC-4-piperidyl)-4(S)-hydroxy]hept-2-ynoate (15b)

A solution of S-Alpine-Borane ® (0.5M in THF, 7.5 mL, 3.8 mmol) was added dropwise to neat ketone 14 (0.66 g, 1.8 mmol) at 0°, then the mixture was warmed to RT. After 2 days acetaldehyde (0.4 mL, 7.2 mmol) was added and allowed to react for 15 minutes before removing the solvent. The resulting mixture was diluted with 10 mL ether, cooled to 0°, ethanolamine (0.25 g, 4.1 mmol) was added, and after 15 minutes the resulting white ppt was removed by filtration. The filtrate was washed with brine, dried (MgSO4), and concentrated. Chromatography (silica, 20% ethyl acetate/hexane) provided S alcohol 15b (0.52 g, 78%) as a colorless oil, $R_f$ 0.35 (30% ethyl acetate/hexane):

$^1$H NMR (300 MHz, CDCl3) δ 4.51 (q, J=5.9 Hz, 1H), 4.26 (q, J=7.1 Hz, 2H), 4.1 (br s, 2H), 2.68 (br t, J=12 Hz, 2H), 2.13 (d, J=5.8 Hz, 1H), 1.82-1.60 (m), 1.60-1.25 (m), 1.47 (s, 9H), 1.34 (t, J=7.1 Hz, 3H), 1.09 (qd, J=12.3, 4.5 Hz, 2H); e.e., 68%.

Preparation of Ethyl [7-(N-BOC-4-piperidyl)-4(S)-(t-butyldimethylsilyloxy)]hept-2-ynoate (16b)

A solution of alcohol 15b (0.496 g, 1.40 mmol) in 7 mL DMF was treated with imidazole (0.248 g, 3.64 mmol) and t-butyldimethylsily chloride (0.275 g, 1.82 mmol). After 3 days the mixture was diluted with ether and washed with 1% HCl, the aqueous layer re-extracted with ether, and the combined organic extracts were washed with 1% HCl, sat. NaHCO3, and brine, dried (MgSO4), and concentrated. Flash chromatography (silica, 7.5% ethyl acetate/hexane) provided S silyl ether 16b (0.343 g, 52%) as a colorless oil.

$R_f$ 0.74 (30% ethyl acetate/hexane).

$^1$H NMR (300 MHz, CDCl3) δ 4.47 (t, J=6.2 Hz, 1H), 4.25 (q, J=7.2 Hz, 2H), 4.1 (br s, 2H), 2.68 (br t, J=12 Hz, 2H), 1.8-1.6 (m, 2H), 1.55-1.25 (m), 1.47 (s, 9H), 1.33 (t, J=7.2 Hz, 3H), 1.08 (qd, J=12.5, 4.0 Hz, 2H), 0.92 (s, 9H), 0.17 (s, 3H), 0.13 (s, 3H).

Preparation of Ethyl [7-(N-BOC-4-piperidyl)-4(S)-(t-butyldimethylsilyloxy)]heptanoate (17b)

A mixture of alkyne 15b (0.343 g, 0.733 mmol) and 10% Pd/C (68 mg) in 5 mL ethyl acetate was held under 1 atm hydrogen for 2.5 hours, then filtered through a Celite pad. Concentration provided 17b (332 mg, 96%) as a colorless oil, $R_f$ 0.39 (10% ethyl acetate/hexane).

$^1$H NMR (300 MHz, CDCl3) δ 4.15 (q, J=7.1 Hz, 2H), 4.1 (br, 2H), 3.72 (qn, J=6.2 Hz, 1H), 2.69 (brt, J=12.5 Hz, 2H), 2.68 (t, J=8.0 Hz, 2H), 1.90-1.65 (m, 4H), 1.48 (s, 9H), 1.5-1.2 (m), 1.28 (t, J=7.1 Hz, 3H), 1.09 (qd, J=12.4, 3.9 Hz, 2H), 0.91 (s, 9H), 0.069 (s, 3H), 0.065 (s, 3H).

Preparation of [7-(N-BOC-4-piperidyl-4(S)-(t-butyldimethylsilyloxy)]-heptanoate (18b)

Sodium hydroxide (1N, 1.03 mL, 1.03 mmol) was added to a solution of ester 17b (324 mg, 0.69 mmol) in 5 mL methanol. After 3 hours additional NaOH (1N, 0.5 mL, 0.5 mmol) was added, then again at 5 hours (1N, 0.5 mL, 0.5 mmol). After stirring over night the yellow solution was concentrated and the residue was diluted with water and washed with ether. The aqueous phase was acidified with 5% KHSO4, extracted twice with ethyl acetate, and the combined extracts were washed with brine before drying (MgSO4) and concentration to yield acid 18b (298 mg, 98%) as a colorless oil, $R_f$ 0.72 (ethyl acetate).

$^1$H NMR (300 MHz, CDCl3) δ 4.1 (br, 2H), 3.741 (qn, J=6.0 Hz, 1H), 2.67 (br, t, J=12 Hz, 2H), 2.44 (t, J=8.2 Hz, 2H), 1.8-1.6 (m, 4H), 1.48 (s, 9H), 1.5-1.2 (m), 1.08 (qd, J=13.4 Hz, 2H), 0.91 (s, 9H), 0.070 (s, 3H), 0.067 (s, 3H).

Preparation of [7-(N-BOC-4-piperidyl)-4(S)-(t-butyldimethylsilyloxy)]heptanoyl-[3(R)-[2-(indol-3-yl)ethyl]β-alanine ethyl ester (19b)

Acid 18b (0.20 g, 0.45 mmol), amine 7 (0.14 g, 0.54 mmol), triethylamine (0.19 mL, 1.4 mmol) and HOBT (79 mg, 0.58 mmol) were combined in 2.2 mL DMF at 0°, EDC (0.11 g, 0.58 mmol) was added and after 10 minutes the reaction was allowed to warm to RT. After stirring over night, the mixture was diluted with ether, washed twice with water, 5% KHSO4, sat. NaHCO3, and brine, dried (MgSO4) and concentrated. Flash chromatography (silica, 40% ethyl acetate/hexane) provided 19b (0.25 g, 81%) as a colorless oil. $R_f$ 0.54 (50% ethyl acetate/hexane):

$^1$H NMR (300 MHz, CDCl3) δ 8.13 (br, s, 1H), 7.60 (d, J=7.8 Hz, 1H), 7.40 (d, J=7.9 Hz, 1H), 7.22 (td, J=8.0, 1.0 Hz, 1H), 7.14 (td, J=7.9, 1.1 Hz, 1H), 7.09 (d, J=2.2 Hz, 1H), 6.17 (d, J=9.0 Hz, 1H), 4.41 (m, 1H), 4.17 (q, J=7.1 Hz, 2H), 4.05 (m, 2H), 3.74 (br qn, J=6.0 Hz, 1H), 2.82 (q, J=8.0 Hz, 2H), 2.67 (br t, J=12 Hz, 2H), 2.60 (apparent t. J=4.8 Hz, 2H), 2.23 (m, 2H), 2.1-1.6 (m, 6H), 1.50 (s, 9H), 1.45-1.2 (m, ), 1.29 (t, J=7.1 Hz, 3H), 1.1 (m, 2H), 0.94 (s 9H), 0.099 (s, 3H), 0.087 (s, 3H).

Preparation of [7-(N-BOC-4-piperidyl)-4(S)-(t-butyldimethylsilyloxy)]heptanoyl-[3(R)-[2-(indol-3-yl)ethyl]β-alanine (20b)

Ester 19b (250 mg, 0.364 mmol) was dissolved in 4 mL methanol, and NaOH (1N, 0.91 mL, 0.91 mmol) was added. After stirring over night solvent was removed and the residue was taken up in water and ether. The pH was adjusted to 1 with 5% KHSO4 and the aqueous phase was extracted again with ether. The combined organic phases were washed with water then brine, dried (MgSO4) and concentrated providing the acid 20b (214 mg, 89%) as a yellow oil, $R_f$ 0.27 (9.5:0.5:0.5, methylene chloride:methanol:acetic acid):

$^1$H NMR (300 MHz, CDCl3) δ 8.18 (br, s, 1H), 7.61 (d, J=7.9 Hz, 1H), 7.39 (d, J=8.1 Hz, 1H), 7.23 (td, J=7.1, 1.5 Hz, 1H), 7.14 (td, J=8.0, 1.2 Hz, 1H), 7.07 (d, J=2.3 Hz, 1H), 6.21 (d, J=4.41 m Hz, 1H), 4.38 (m, 1), 4.1 (br 2), 3.74 (br m, 1H), 2.88 (m, 2H), 2.8-2.6 (m, 4H), 2.35-2.0 (m), 1.9-1.6 (m), 1.50 (s, 9H), 1.5-1.3 (m), 1.1 (m, 2H), 0.94 (s, 9H), 0.098 (s, 3H), 0.089 (s, 3H).

Preparation of [7-(4-piperidyl)-4(S)-(t-butyldimethylsilyloxy)]heptanoyl-[3(R)-[2-(indol-3-yl)ethyl]β-alanine (21b)

Acid 20b (214 mg, 0.32 mmol) was dissolved in 1.6 mL methylene chloride along with anisole (71 μL, 0.65 mmol) and cooled to −15°. TFA (1.6 mL) was added and after 20 minutes the solvents were removed. Flash chromatography (silica, 10:0.9:0.9, EtOH:conc NH₄OH:water) provided a colorless glass which was triturated with ether. Flash chromatography twice more (silica, 10:0.7:0.7, EtOH:conc NH₄OH:water) and lyophilization provided tripeptide 21b (75 mg, 52%) as a white fluffy solid, $R_f$ 0.23 (10:1:1 EtOH:conc. NH₄OH:H₂O):

¹H NMR (400 MHz, D₂O) δ7.8 (d, J=7.5 Hz, 1H), 7.41 (d, J=8.1 Hz, 1H), 7.15 (t, J=7.1 Hz, 1H), 7.12 (s, 1H), 7.06 (t, J=7.1 Hz, 1H), 4.12 (m, 1H), 3.50 (m, 1H), 3.19 (br d, J=12 Hz, 2H), 2.75-2.65 (m, 4H), 2.31 (ABX,2H), 2.20-2.10 (m, 2H), 1.91 (m, 1H), 1.79 (m, 1H), 1.70-1.50 (m, 4H), 1.36-1.05 (m, 8H).

Preparation of N-BOC-4-piperidineethyl iodide (22)

To a stirring solution of 9 (18.0 g, 77 mmol), triphenylphosphine (22.2 g, 85 mmol), imidazole (7.9 g, 115 mmol), and benzene (800 mL) at ambient temperature was added iodine (22.0 g, 85 mmol). After 5 min the heterogeneous reaction mixture was filtered and the filtrate concentrated. Flash chromatography (silica gel, 10% ethyl acetate/hexanes) gave 22 (20 g, 59%) as an oil.

TLC Rf=0.95 (50% ethyl acetate/hexanes).

¹H NMR (300 MHz, CDCl₃) δ4.11 (m, 2H), 3.24 (t, J=6 Hz, 2H), 2.72 (m, 2H), 1.82 (dt, J=7, 7 Hz, 2H), 1.75, −1.55 (m, 5H), 1.48 (s, 9H), 1.12 (m, 2H).

Preparation of N-BOC-4-piperidineethyl azide (23)

A solution of 22 (5.0 g, 14.7 mmol), DMSO (75 mL), and NaN₃ (1.9 g, 29.4 mmol) was heated at 70° C. for 2 hr. The cooled reaction mixture was diluted with ethyl acetate and then washed with water (2×) and brine, dried (MgSO₄), and concentrated to afford 23 (3.6 g, 96%) as a colorless oil.

TLC Rf=0.75 (30% ethyl acetate/hexanes).

¹H NMR (300 MHz, CDCl₃) δ4.11 (m, 2H), 3.36 (t, J=7 Hz, 2H), 2.73 (m, 2H), 1.70 (m, 3H), 1.49 (s, 9H), 1.15 (m, 2H).

Preparation of N-BOC-4 piperidineethyl amine (24)

A mixture of 23 (1.1 g, 4.3 mmol), 10% Pd/C (0.16 g), and ethanol was stirred under a hydrogen atmosphere (1 atm) for 1.5 hr. The reaction mixture was then filtered through a celite pad and the filtrate concentrated to give crude 24 (1.0 g) as an oil.

TLC Rf=0.18 (9:1:1 CH₂CH₂/CH₃OH/HOAc).

¹H NMR (300 MHz, CDCl₃) δ4.10 (m, 2H), 2.78 (t, J=7 Hz, 2H), 2.70 (m, 2H), 1.80 (m, 2H), 1.67 (m, 2H), 1.52 (m, 1H), 1.47 (s, 9H), 1.17 (m, 2H).

Preparation of N-BOC-4-piperidineethylaminesuccinic acid (25)

To a stirred solution of amine 24 (0.55 g, 2.4 mmol) and CH₃CN(25 mL) at ambient temperature was added succinic anhydride (0.24 g, 2.4 mmol). After 3.0 h the reaction mixture was concentrated. Flash chromatography (silica, 97:3:1 CHCl₃/CH₃OH/HOAc) gave 25(0.66 g, 83%) as a colorless oil.

TLC Rf=0.80 (9:1:1 CH₂Cl₂/CH₃OH/HOAc)

Preparation of N-BOC-4-piperidineethylamine-Suc[3(R)-[2-(indol-3-yl)ethyl]β-alanine ethyl ester (26)

To a stirred solution of 25 (111 mg, 0.34 mmol), ethyl acetate (10 mL), and NMM (35 μL, 0.30 mmol) at 0° C. was added i-butyl chloroformate (0.34 mmol), and after stirring for 15 minutes, amine 7 (80 mg, 0.31 mmol) was added the free base. After 20 h the reaction was diluted with ethyl acetate and then washed sequentially with 10% KHSO₄, H₂O, sat. NaHCO₃ and brine, dried (MgSO₄), and concentrated. Flash chromatography (silica, 3% CH₃OH/CHCl₃ gave 26 (119 mg, 69%) as an oil.

TLC R$_f$=0.22 (5% CH₃OH/CHCl₃).

¹H NMR (300 MHz, CDCl₃) δ8.76 (bs, 1H), 7.53(d), J=7 Hz,1H), 7.31 (d, J=7 Hz,1H), 7.13(t, J=7 Hz,1H), 7.04(t, J=7 Hz,1H), 6.95(bs,1H),6.72 (d, J=8 Hz,1H), 6.49(m,1H), 4.34(m,1H), 4.10(q, J=7 Hz,2H), 4.01 (m,2H), 3.16 (m,2H), 2.76 (m,2H), 2.70-2.40(m,10H), 1.92 (m,2H), 1.52(m,3H), 1.48(s,9H), 1.30(m,3H), 1.23 (t,J=7 Hz,3H), 1.00 (m,2H).

Preparation of N-BOC-4-piperidineethylamine-Suc-[3(R)-[2-(indol-3-yl)ethyl]β-alanine (27).

A mixture of 26 (118 mg, 0.21 mmol), 1N NaOH (5 mL), and CH₃OH(5 mL) was stirred at ambient temperature for 2 h, followed by concentration. The residue was diluted with ethyl acetate and then washed with 5% KHSO₄ and brine, dried (MgSO₄) and concentrated to give 27 (101 mg, 89%) as an oil.

TLC R$_f$=0.61 (9:1:1 Ch₂Cl₂/CH₃OH/HOAC).

Preparation of 4-piperidineethylamine-Suc-[3(R)-[2-(indol-3-yl)ethyl]β-alanine (28)

Compound 27 (101 mg, 0.19 mmol) was converted to 28 (56 mg, 67%) using the same procedure for converting 20a to 21a.

TLC R$_f$=0.17 (9:1:1 ethanol/H₂O/conc. NH₄OH);
¹HNMR 300 MHz, CD₃OD) δ7.59 (d, J=7 Hz, 1H), 7.38 (d, J=7 Hz, 1H), 7.12 (t, J=7 Hz, 1H), 7.10 (s,1H), 7.03 (t, J=7 Hz, 1H), 4.25(m,1H), 3.26 (bd, 2H), 3.17(m,2H), 2.90-2.70 (m,4H), 2.49(bs, 4H), 2.40 (d,2H), 2.05-1.70(m, 4H), 1.60-1.20 (m,6H).

Applicants hereby incorporate by reference procedures for preparing compounds of the present invention whereby guanidines are prepared from amines and whereby amidines are prepared from corresponding nitriles. Guanidines may be prepared from amines by those having ordinary skill in the art upon reaction with 3,5-dimethylpyrazole-1-carboxamidine nitrate (*Methods Enzymol.*, 25b, 558, 1972). Amidines may be prepared from the corresponding nitrile by those having ordinary skill in the art using procedures demonstrated by Boere, R. T., et. al. *J. Organomet. Chem.*, 331(2), 161-7, 1987; and Fuks, R., *Tetrahedron*, 29 (14), 2147-51, 1973.

Utilizing the methodology demonstrated in this invention, the following compounds, included in Table I below, are exemplary of the compounds which may be prepared according to this invention.

TABLE I
$$R^1-CH_2-\overset{\overset{O}{\|}}{C}-NH-R^2$$
| R¹ | R² |
|---|---|
| 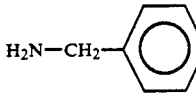 | 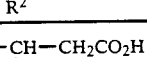 |
| 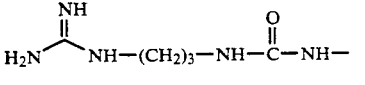 | 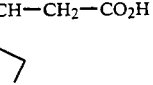 |
| 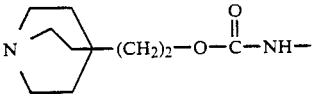 | 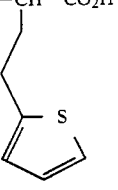 |
| 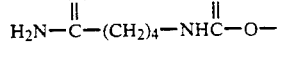 | 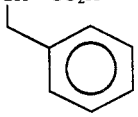 |
| 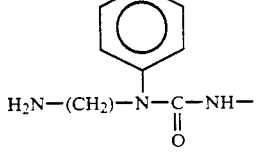 | $-CH_2-CH_2CO_2H$ |
| 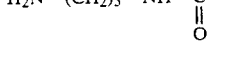 | 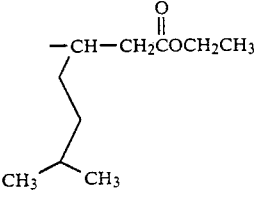 |
| 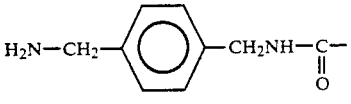 | $-CH_2CH_2CO_2H$ |
| 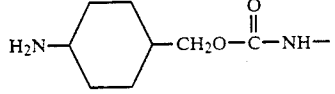 | 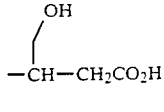 |

TABLE I-continued

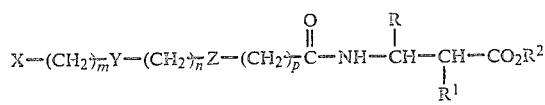

| $R^1$ | $R^2$ |
|---|---|
| $H_2N-(CH_2)_5-\overset{CH_3}{\underset{\underset{O}{\|}}{N}}-\overset{CH_2CH_3}{\underset{}{C}}-N$ | $-CH_2CH_2\overset{O}{\overset{\|}{C}}OCH_2\overset{O}{\overset{\|}{C}}-CH(CH_3)_2$ |

What is claimed is:

1. A fibrinogen receptor antagonist of Formula I:

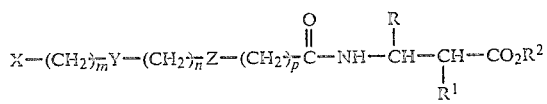

wherein:

X is

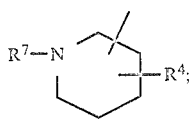

Y is

$R^4 = R^5 = R^6 = R^7 = $ hydrogen;

R and $R^1$ are independently chosen from phenyl$C_{1-3}$alkyl, indole$C_{1-3}$alkyl, or hydrogen, provided both R and $R^1$ are not simultaneously hydrogen;

$R^2$ is hydrogen, $C_{1-12}$alkyl, unsubstituted of substituted with one or more $C_{1-6}$alkyl groups,

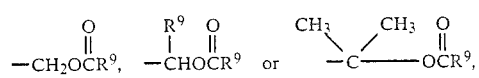

wherein $R^9$ is $C_{1-6}$alkyl branched or unbranched or phenyl, and wherein when $R^9$, when appearing more than once, can be the same or different,;

m is 1–10;
n is 0–9;
p is 1 or 2;
Z is

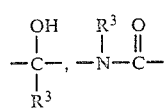

where $R^3$ is hydrogen or $C_{1-4}$alkyl unsubstituted or substituted with one or more $C_{1-4}$alkyl or phenyl group unsubstituted or optionally substituted with one or more groups selected from hydroxyl, halogen, cyano, trifluromethyl, $C_{1-3}$alkoxy, $C_{1-5}$alkylcarbonyloxy, $C_{1-5}$alkoxycarbonyl, $C_{1-5}$alkyl, amino$C_{1-5}$alkyl, hydroxycarbonyl$C_{0-5}$alkyl, or hydroxycarbonyl$C_{1-5}$alkoxy;

or the pharmaceutically acceptable salts thereof, or optical isomers thereof.

2. A fibrinogen receptor antagonist of claim 1 having the formula:

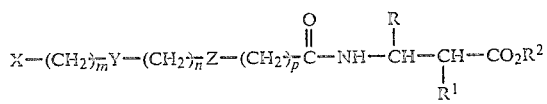

wherein:

X is

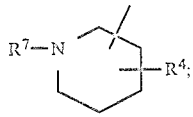

Y is

$R^4 = R^5 = R^6 = R^7 = $ hydrogen;

R and $R^1$ are independently chosen from phenyl$C_{1-3}$alkyl, indole$C_{1-3}$alkyl, or hydrogen, provided both R and $R^1$ are not simultaneously hydrogen;

$R^2$ is hydrogen;

$C_{1-12}$alkyl, unsubstituted of substituted with one or more $C_{1-6}$alkyl groups,

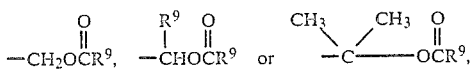

wherein $R^9$ is $C_{1-6}$alkyl branched or unbranched or phenyl, and wherein when $R^9$, when appearing more than once, can be the same or different, m is 1–5;
n is 0–4;
p is 1 or 2;
Z is

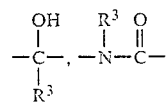

where $R^3$ is hydrogen or $C_{1-4}$alkyl unsubstituted or substituted with one or more $C_{1-4}$alkyl or phenyl group unsubstituted or optionally substituted with one or more groups selected from hydroxyl, halogen, cyano, trifluromethyl, $C_{1-3}$alkoxy, $C_{1-5}$alkylcarbonyloxy, $C_{1-5}$alkoxycarbonyl, $C_{1-5}$alkyl, amino$C_{1-5}$alkyl, hydroxycarbonyl$C_{0-5}$alkyl, or hydroxycarbonyl$C_{1-5}$alkoxy;

or the pharmaceutically acceptable salts thereof, or optical isomers thereof.

3. A fibrinogen receptor antagonist of claim 2 having the formula:

$$X-(CH_2)_{m}Y-(CH_2)_{n}Z-(CH_2)_{p}\overset{O}{\overset{\|}{C}}-NH-\overset{R}{\underset{R^1}{\overset{|}{C}H}}-CH-CO_2R^2 \quad I$$

wherein:
X is $$R^7-N\diagup\hspace{-1em}\diagdown R^4;$$

Y is $$-\overset{R^6}{\underset{R^5}{\overset{|}{C}}}-;$$

$R^4 = R^5 = R^6 = R^7 =$ hydrogen;
R and $R^1$ are independently chosen from phenyl$C_{1-3}$alkyl, indole$C_{1-3}$alkyl, or hydrogen, provided both R and $R^1$ are not simultaneously hydrogen;
$R^2$ is
hydrogen;
$C_{1-12}$alkyl, unsubstituted of substituted with one or more $C_{1-6}$alkyl groups, $$-CH_2O\overset{O}{\overset{\|}{C}}R^9, \quad -\overset{R^9}{\underset{}{\overset{|}{C}H}}O\overset{O}{\overset{\|}{C}}R^9, \quad or \quad -\overset{CH_3}{\underset{}{\overset{\diagup}{C}}}\overset{CH_3}{\underset{}{\diagdown}}-O\overset{O}{\overset{\|}{C}}R^9,$$

wherein $R^9$ is $C_{1-6}$alkyl branched or unbranched or phenyl, and wherein when $R^9$, when appearing more than once, can be the same or different;
m is 1–5;
n is 0–4;
p is 1 or 2;
Z is $$-\overset{OH}{\underset{R^3}{\overset{|}{C}}}-, \quad -\overset{R^3}{\underset{}{\overset{|}{N}}}-\overset{O}{\overset{\|}{C}}-$$

where $R^3$ is hydrogen or $C_{1-4}$alkyl unsubstituted or substituted with one or more $C_{1-4}$alkyl or phenyl group unsubstituted or optionally substituted with one or more groups selected from hydroxyl, halogen, cyano, trifluromethyl, $C_{1-3}$alkoxy, $C_{1-5}$alkylcarbonyloxy, $C_{1-5}$alkoxycarbonyl, $C_{1-5}$alkyl, amino$C_{1-5}$alkyl, hydroxycarbonyl$C_{0-5}$alkyl, or hydroxycarbonyl$C_{1-5}$alkoxy;

or the pharmaceutically acceptable salts thereof, or optical isomers thereof.

4. A compound of claim 1 selected from the group consisting of:

and

5. A pharmaceutical composition for inhibiting the binding of fibrinogen to blood platelets in a mammal, comprising an effective amount of a compound of claim 1 and a pharmaceutically acceptable carrier.

6. A solid composition for preventing thrombus or embolus formation in a mammal by inhibiting the binding of fibrinogen to blood platelets, comprising an effective amount of a compound of claim 1 and a pharmaceutically acceptable carrier.

7. A liquid composition for treating thrombus or embolus formation in a mammal by inhibiting the binding of fibrinogen to blood platelets, comprising an effective amount of a compound of claim 1 and a pharmaceutically acceptable carrier.

8. A method for preventing thrombus or embolus formation in a mammal by inhibiting the binding of fibrinogen to blood platelets, comprising orally administering to the mammal the composition of claim 6.

9. A method for treating thrombus or embolus formation in a mammal by inhibiting the binding of fibrinogen to blood platelets, comprising intravenously administering to the mammal the composition of claim 7.

* * * * *